United States Patent
Wang et al.

(10) Patent No.: US 9,739,741 B2
(45) Date of Patent: Aug. 22, 2017

(54) TUBE-IN-A-TUBE ELECTRONIC SENSORS

(71) Applicants: YuHuang Wang, Laurel, MD (US); Jia Huang, Shanghai (CN); Allen Ng, Silver Spring, MD (US); Yanmei Piao, College Park, MD (US); Cheng S. Lee, Ellicott City, MD (US)

(72) Inventors: YuHuang Wang, Laurel, MD (US); Jia Huang, Shanghai (CN); Allen Ng, Silver Spring, MD (US); Yanmei Piao, College Park, MD (US); Cheng S. Lee, Ellicott City, MD (US)

(73) Assignee: UNIVERSITY OF MARYLAND, COLLEGE PARK, College Park, MD (US)

(*) Notice: Subject to any disclaimer, the term of this patent is extended or adjusted under 35 U.S.C. 154(b) by 416 days.

(21) Appl. No.: 14/213,015

(22) Filed: Mar. 14, 2014

(65) Prior Publication Data
US 2014/0342949 A1  Nov. 20, 2014

Related U.S. Application Data

(60) Provisional application No. 61/782,867, filed on Mar. 14, 2013.

(51) Int. Cl.
| | | |
|---|---|---|
| G01N 27/327 | (2006.01) | |
| C12Q 1/68 | (2006.01) | |
| G01N 27/22 | (2006.01) | |
| G01N 33/543 | (2006.01) | |
| B01J 19/12 | (2006.01) | |
| G01N 33/00 | (2006.01) | |

(52) U.S. Cl.
CPC .......... *G01N 27/227* (2013.01); *B01J 19/121* (2013.01); *G01N 33/54373* (2013.01); *G01N 33/0057* (2013.01)

(58) Field of Classification Search
None
See application file for complete search history.

(56) References Cited

U.S. PATENT DOCUMENTS

| | | | | |
|---|---|---|---|---|
| 7,794,683 | B1* | 9/2010 | Forohar | B82Y 30/00 423/447.1 |
| 2004/0071624 | A1* | 4/2004 | Tour | B82Y 30/00 423/447.1 |
| 2006/0228723 | A1* | 10/2006 | Bradley | B01L 3/50857 435/6.11 |
| 2009/0306427 | A1* | 12/2009 | Martinez-Rubi | B82Y 30/00 562/590 |
| 2011/0262729 | A1* | 10/2011 | Chen | B82Y 30/00 428/221 |

(Continued)

OTHER PUBLICATIONS

Baughman, R.H. et al., "Carbon Nanotubes—the Route Toward Applications," *Science* 297:787-792, American Association for the Advancement of Science (2002).

(Continued)

*Primary Examiner* — Robert T Crow
(74) *Attorney, Agent, or Firm* — Sterne, Kessler, Goldstein & Fox P.L.L.C.

(57) ABSTRACT

The present invention is directed to tube-in-a-tube electronic materials and electronic chemical sensors comprising tube-in-a-tube configurations such as covalently functionalized double-walled carbon nanotubes.

12 Claims, 15 Drawing Sheets

(56) References Cited

U.S. PATENT DOCUMENTS

2011/0269243 A1* 11/2011 Strano .................... B82Y 30/00
436/172

OTHER PUBLICATIONS

Blanksby, S.J. and Ellison, G.B., "Bond Dissociation Energies of Organic Molecules," *Acc. Chem. Res. 36*:255-263, American Chemical Society (2003).

Bouilly, D. et al., "Wall-Selective Probing of Double-Walled Carbon Nanotubes Using Covalent Functionalization," *ACS Nano 5*:4927-4934, American Chemical Society (2011).

Bronzena, A.H. et al., "Outer Wall Selectively Oxidized, Water-Soluble Double-Walled Carbon Nanotubes," *J. Am. Chem. Soc. 132*:3932-3938, American Chemical Society (2010).

Burgener, M. et al., "Synthesis of a Stable and Specific Surface Plasmon Resonance Biosensor Surface Employing Covalently Immobilized Peptide Nucleic Acids," *Bioconjugate Chem. 11*:749-754, American Chemical Society (2000).

Cao, Q. and Rogers, J.A., "Ultrathin Films of Single-Walled Carbon Nanotubes for Electronics and Sensors: A Review of Fundamental and Applied Aspects," *Adv. Mater. 21*:29-53, Wiley-VCH Verlag GmbH & Co. KGaA, Weinheim (2009).

Chen, R.J. et al., "Noncovalent functionalization of carbon nanotubes for highly specific electronic biosensors," *PNAS 100*:4984-4989, National Academy of Sciences (2003).

Deng, S. et al., "Outerwall selective alkylcarboxylation and enrichment of double-walled carbon nanotubes," *J. Mater. Chem. 21*:18568-18574, The Royal Society of Chemistry (2011).

Dresselhaus, M.S. et al., "Raman Spectroscopy of Carbon Nanotubes in 1997 and 2007," *J. Phys. Chem. C 111*:17887-17893, American Chemical Society (2007).

Dungchai W. et al., "Electrochemical Detection for Paper-Based Microfluidics," *Anal. Chem. 81*:5821-5826, American Chemical Society (2009).

Endo, M. et al., "'Buckypaper' from coaxial nanotubes," *Nature 433*:476, Nature Publishing Group (2005).

Forzani, E.S. et al., "Tuning the Chemical Selectivity of SWNT-FETs for Detection of Heavy-Metal Ions," *Small 2*:1283-1291, Wiley-VCH Verlag GmbH & Co. KGaA, Weinheim (2006).

Ganzhorn, M. et al., "Hydrogen Sensing with Diameter- and Chirality-Sorted Carbon Nanotubes," *ACS Nano 5*:1670-1676, American Chemical Society (2011).

Goldsmith, B.R. et al., "Conductance-Controlled Point Functionalization of Single-Walled Carbon Nanotubes," *Science 315*:77-81, American Association for the Advancement of Science (2007).

Green, A.A. and Hersam, M.C., "Processing and properties of highly enriched double-wall carbon nanotubes," *Nat. Nanotechnol. 4*:64-70, Macmillan Publishers Limited (2009).

Green, A.A. and Hersam, M.C., "Properties and Application of Double-Walled Carbon Nanotubes Sorted by Outer-Wall Electronic Type," *ACS Nano 2*:1459-1467, American Chemical Society (2011).

Gui, E.L. et al., "DNA Sensing by Field-Effect Transistors Based on Networks of Carbon Nanotubes," *J. Am. Chem. Soc. 129*:14427-14432, American Chemical Society (2007).

Heller, I. et al., "Identifying the Mechanism of Biosensing with Carbon Nanotube Transistors," *Nano Lett. 8*:591-595, American Chemical Society (2008).

Huang, J. et al., "Covalently Functionalized Double-Walled Carbon Nanotubes Combine High Sensitivity and Selectivity in the Electrical Detection of Small Molecules," *J. Am. Chem. Soc. 135*:2306-2312, American Chemical Society (Jan. 17, 2013).

Ionescu, R.E. et al., "Impedimetric immunosensor for the specific label free detection of ciprofloxacin antibiotic," *Biosens. Bioelectron. 23*:549-555, Elsevier B.V. (2007).

Jariwala, D. et. al., "Carbon nanomaterials for electronics, optoelectronics, photovoltaics, and sensing," *Chem. Soc. Rev. 42*:2824-2860, The Royal Society of Chemistry (Apr. 7, 2013).

Kang, S.J. et al., "High-performance electronics using dense, perfectly aligned arrays of single-walled carbon nanotubes," *Nat. Nanotechnol. 2*:230-236, Nature Publishing Group (2007).

Kim, J.P. et al., "Untrasensitive carbon nanotube-based biosensors using antibody-binding fragments," *Anal. Biochem, 381*:193-198, Elsevier Inc. (2008).

Kim, T.H. et al., "Selective and Sensitive TNT Sensors Using Biomimetic Polydiacetylene-Coated CNT-FETs," *ACS Nano 5*:2824-2830, American Chemical Society (2011).

Kim, T.H. et al., "Single-Carbon-Atomic-Resolution Detection of Odorant Molecules using a Human Olfactory Receptor-based Bioelectronic Nose," *Adv. Mater. 21*:91-94, Wiley-VCH Verlag GmbH & Co. KGaA, Weinheim (2009).

Kong. J. et al., "Nanotube Molecular Wires as Chemical Sensors," *Science 287*:622-625, American Association for the Advancement of Science (2000).

Li, C. et. al., "Complementary Detection of Prostate-Specific Antigen Using $In_2O_3$ Nanowires and Carbon Nanotubes," *J. Am. Chem. Soc. 127*:12484-12485, American Chemical Society (2005).

Liu, K. et al., "Chirality-Dependent Transport Properties of Double-Walled Nanotubes Measured in Situ on Their Field-Effect Transistors," *J. Am. Chem. Soc. 131*:62-63, American Chemical Society (2009).

Mao, S. et al., "Specific biosensing using carbon nanotubes functionalized with gold nanoparticle-antibody conjugates," *Carbon 48*:479-486, Elsevier Ltd. (2009).

Martinez, A.W. et al., "Diagnostics for the Developing World: Microfluidic Paper-Based Analytical Devices," *Anal. Chem. 82*:3-10, American Chemical Society (2010).

Martinez, A.W. et al., "Patterned Paper as a Platform for Inexpensive, Low-Volume, Portable Bioassays," *Angew. Chem. Int. Ed. 46*:1318-1320, Wiley-VCH Verlag GmbH & Co. KGaA, Weinheim (2007).

Martinez, M.T. et al., "Label-Free DNA Biosensors Based on Functionalized Carbon Nanotube Field Effect Transistors," *Nano Lett. 9*:530-536, American Chemical Society (2009).

Meric, I. et al., "Current saturation in zero-bandgap, top-gated graphene field-effect transistors," *Nat. Nanotechnol. 3*:654-659, Macmillan Publishers Limited (2008).

Myung, S. et al., "Graphene-Encapsulated Nanoparticle-Based Biosensor for the Selective Detection of Cancer Biomarkers," *Adv. Mater. 23*:2221-2225, Wiley-VCH Verlag GmbH & Co. KGaA, Weinheim (2011).

Myung, S. et al., "Label-Free Polypeptide-Based Enzyme Detection using a Graphene-Nanoparticle Hybrid Sensor," *Adv. Mater. 24*:6081-6087, Wiley-VCH Verlag GmbH & Co. KGaA, Weinheim (Nov. 27, 2012).

O'Connell, M.J. et al., "Band Gap Fluorescence from Individual Single-Walled Carbon Nanotubes," *Science 297*:593-596, American Association for the Advancement of Science (2002).

Pacios, M. et al., "Real time protein recognition in a liquid-gated carbon nanotube field-effect transistor modified with aptamers," *Nanoscale 4*:5917-5923, The Royal Society of Chemistry (Sep. 28, 2012).

Piao, Y. et al., "Optical and Electrical Properties of Inner Tubes in Outer Wall-Selectively Functionalized Double-Wall Carbon Nanotubes," *J. Phys. Chem. Lett. 2*:1577-1582, American Chemical Society (2011).

Qi, H. et al., "Synthesis of Uniform Double-Walled Carbon Nanotubes Using Iron Disilicide as Catalyst," *Nano Lett. 7*:2417-2421, American Chemical Society (2007).

Quhe, R. et al., "Tunable and sizable band gap of single-layer graphene sandwiched between hexagonal boron nitride," *NPG Asia Mater. 4*:1-10, Nature Japan K.K. (published online Feb. 17, 2012).

Roberts, M.E. et al., "Sorted and Aligned Single-Walled Carbon Nanotube Networks for Transistor-Based Aqueous Chemical Sensors," *ACS Nano 3*:3287-3293, American Chemical Society (2009).

Robinson, J.T. et al., "Properties of Fluorinated Graphene Films," *Nano Lett. 10*:3001-3005, American Chemical Society (2010).

Shen, C. et al., "Double-walled carbon nanotubes: Challenges and opportunities," *Nanoscale 3*:503-518, The Royal Society of Chemistry (2011).

(56) References Cited

OTHER PUBLICATIONS

Sinnokrot, M.O. et al., "Estimates of the Ab Initio Limit for π-π Interactions: The Benzene Dimer," *J. Am. Chem. Soc. 124*:10887-10893, American Chemical Society (2002).

Sorgenfrei, S. et al., "Label-free single-molecule detection of DNA-hybridization kinetics with a carbon nanotube field-effect transistor," *Nat. Nanotechol. 6*:126-132, Macmillan Publishers Limited (2011).

Star, A. et al., "Interaction of Aromatic Compounds with Carbon Nanotubes: Correlation to the Hammett Parameter of the Substituent and Measured Carbon Nanotube FET Response," *Nano Lett. 3*:1421-1423, American Chemical Society (2003).

Star, A. et al., "Label-free detection of DNA hybridization using carbon nanotube network field-effect transistors," *PNAS 103*:921-926, The National Academy of Sciences (2006).

Sun, D.-m. et al., "Flexible high-performance carbon nanotube integrated circuits," *Nat. Nanotechnol. 6*:156-161, Macmillan Publishers Limited (2011).

Takeda, S. et al., "Application of carbon nanotubes for detecting anti-hemagglutinins based on antigen-antibody interaction," *Biosens. Bioelectron. 21*:201-205, Elsevier B.V. (2005).

Tey, J.N. et al., "Direct Detection of Heroin Metabolites Using a Competitive Immunoassay Based on a Carbon-Nanotube Liquid-Gated Field-Effect Transistor," *Small 6*:993-998, Wiley-VCH Verlag GmbH & Co. KGaA, Weinheim (2010).

Villalpando-Paez, F. et al., "Raman Spectroscopy Study of Isolated Double-Walled Carbon Nanotubes with Different Metallic and Semiconducting Configurations," *Nano Lett. 8*:3879-3886, American Chemical Society (2008).

Wang, F. and Swager, T.M., "Diverse Chemiresistors Based upon Covalently Modified Multiwalled Carbon Nanotubes," *J. Am. Chem. Soc. 133*:11181-11193, American Chemical Society (2011).

Wu, Z. et al., "Transparent, Conductive Carbon Nanotube Films," *Science 305*:1273-1276, American Association for the Advancement of Science (2004).

Zheng, G. et al., "Multiplexed electrical detection of cancer markers with nanowire sensor arrays," *Nat. Biotechnol. 23*:1294-1301, Nature Publishing Group (2005).

Peng, N. et al., "Sensing Mechanisms for Carbon Nanotube Based $NH_3$ Gas Detection," *Nano Lett. 9*:1626-1630, American Chemical Society (2009).

Park, H. et al., "Effects of Sidewall Functionalization on Conducting Properties of Single Wall Carbon Nanotubes," *Nano Lett. 6*:916-919, American Chemical Society (2006).

* cited by examiner

TUBE-IN-A-TUBE ELECTRONIC SENSORS

STATEMENT REGARDING FEDERALLY SPONSORED RESEARCH OR DEVELOPMENT

This invention was made with support from the National Science Foundation under award number CHE1055514 and the Office of Naval Research under award number N000141110465. The government has certain rights to this invention.

BACKGROUND OF THE INVENTION

Field of the Invention

The present disclosure relates generally to tube-in-a-tube (Tube^2) electronic materials and electronic chemical sensors comprising Tube^2.

Background

One of the challenges and opportunities in nanoscience lies in developing the ability to utilize the electrical properties of nanomaterials in complex chemical systems such as solar cells, fuel cells, microprocessors, and sensors. In the context of sensing applications, there is hope that nanomaterials will allow for fabrication of electrical sensors capable of detecting ultralow concentrations of analytes, e.g., explosives (such as TNT, nitroglycerin, cyclotetramethylene-tetranitramine) and biomolecules (such as HIV), with ultrahigh selectivity such that trace interferents will not trigger false positives. Various nanostructures and strategies have been explored for meeting this challenge. Some of the most sensitive sensors are based on graphene and pristine single-walled carbon nanotubes (SWCNTs) (Kong et al., *Science* 2000, 287, 622; Chen et al., *Proc. Nat. Acad. Sci. U.S.A.* 2003, 100, 4984; Star et al., *Proc. Natl. Acad. Sci. U.S.A.* 2006, 103, 921; Sorgenfrei, et al., *Nat. Nanotechnol.* 2011, 6, 126; Kim, et al., *Adv. Mater.* 2009, 21, 91; Li et al., *J. Am. Chem. Soc.* 2005, 127, 12484; Ganzhorn et al., *ACS Nano* 2011, 5, 1670; Cao et al., *Adv. Mater.* 2009, 21, 29; Kim, et al., *ACS Nano* 2011, 5, 2824; Forzani, et al., *Small* 2006, 2, 1283; Roberts et al., *ACS Nano* 2009, 3, 3287; Myung et al., *Adv. Mater.* 2011, 23, 2221; and Myung, et al., *Adv. Mater.* 2012, 24, 6081).

Some success has also been achieved with non-covalent functionalization of the surface with receptor molecules to overcome non-specific binding. (Chen et al., *Proc. Nat. Acad. Sci. U.S.A.* 2003, 100, 4984; Martinez et al., *Nano Lett.* 2009, 9, 530; and Pacios et al., *Nanoscale* 2012, 4, 5917). However, low long-term stability and incomplete surface coverage of non-covalent coatings remain general concerns for more demanding applications such as in vivo studies and those involving more aggressive chemical reactions that require a more stable and robust platform (Wang, et al., *Am. Chem. Soc.* 2011, 133, 11181). Covalent attachment of receptor molecules to the surface is an effective strategy for improving chemical selectivity. But the number of functional groups that can be covalently attached to a SWCNT sidewall or graphene surface is limited since covalent modifications quickly destroy their electrical properties (Goldsmith et al., *Science* 2007, 315, 77).

A double-walled carbon nanotube (DWCNT) consists of two concentric SWCNTs that exhibit complicated but relatively independent electronic properties (Shen et al., *Nanoscale* 2011, 3, 503). Field-effect transistors integrating individual, pristine DWCNTs have been shown to have high on/off ratios (>$10^3$) and exceptional conductivity (Liu et al., *J. Am. Chem. Soc.* 2009, 131, 62 and Bouilly et al., *ACS Nano* 2011, 5, 4927). Advances in synthesis (Endo et al., *Nature* 2005, 433, 476 and Qi et al., *Nano Lett.* 2007, 7, 2417) and purification of DWCNTs (Green et al., *Nat. Nanotechnol.* 2009, 4, 64 and Green et al., *ACS Nano* 2011, 5, 1459) have made it possible to fabricate high quality thin film devices. Particularly, recent experiments have shown that the electrical properties of inner tubes can be retained even after heavy functionalization of the outer wall by covalent chemistries (Bouilly et al., *ACS Nano* 2011, 5, 4927; Brozena, et al., *J. Am. Chem. Soc.* 2010, 132, 3932; and Piao et al., *J. Phys. Chem. Lett.* 2011, 2, 1577).

There exists a need for thin-film transistor chemical sensors having ultrahigh selectivity and sensitivity for the electrical detection of biomolecules and other chemicals.

BRIEF SUMMARY OF THE INVENTION

In one aspect, the disclosure provides an electronic chemical sensor comprising: a) a semiconductor transducer; and b) a functional shell in a tube-in-a-tube configuration.

In another aspect, the disclosure provides an electronic chemical sensor comprising: a) a semiconductor transducer; and b) a functional shell in a tube-in-a-tube configuration, wherein the functional shell has an atom-thick backbone with one or more covalently attached functional groups.

In another aspect, the disclosure provides a method, e.g., an optical patterning technique, of removing covalently attached functional groups from the functional shell of a tube-in-a-tube configuration and then re-functionalizing to recover the tube-in-a-tube configurations in a patterned array, the method comprising using a laser or other light source that is resonant with the inner tube of the tube-in-a-tube configuration.

DETAILED DESCRIPTION OF THE INVENTION

Figure 1:
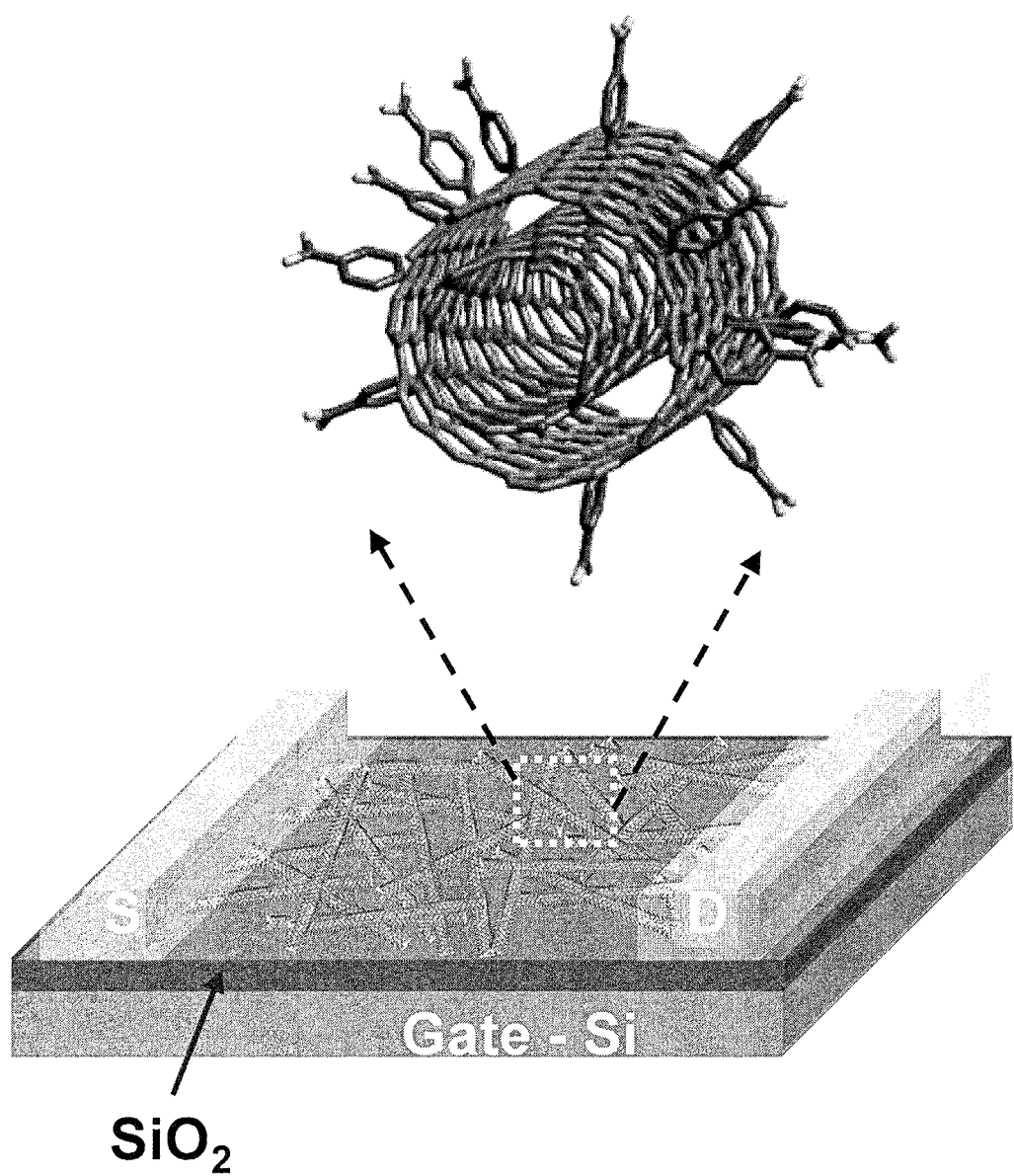
FIG. 1 is a schematic diagram of Tube^2 sensor platform that combines semiconducting inner tubes as transducer elements and chemically tailored outer walls for improved chemical selectivity.

In one embodiment, the disclosure provides an electronic chemical sensor comprising: a) a semiconductor transducer; and b) a functional shell having an atom-thick backbone with one or more types of covalently attached functional groups in a tube-in-a-tube configuration. In another embodiment, the functional groups are selected from the group consisting of —$C_6H_4$—$CO_2H$, —$C_6H_4$—OH, —$C_6H_4$—$CH_3$, —$C_6H_4$—$NO_2$, —$C_6H_4CO_2H$, —$C_6H_4OH$, —$C_6H_4CH_3$, —$C_6H_4NO_2$, —$C_6H_5$, —$C_6H_4C(CH_3)_3$, —$C_6F_4CO_2H$, —$C_6H_2F_3$, —$C_6H_4F$, —$C_6H_4OCH_3$, —$C_6H_4N(CH_3)_2$, —$C_6H_4NO_2$, and —$C_6H_4N(C_2H_5)_2$, or their derivatives.

In another embodiment, the disclosure provides an electronic chemical sensor comprising: a) a semiconductor transducer; and b) a functional shell having an atom-thick backbone with one or more types of covalently attached functional groups in a tube-in-a-tube configuration, and wherein the covalently attached functional groups bind an analyte selectively. In another embodiment, analyte is selected from the group consisting of $NH_3$, $NH_2PhNH_2$, $CH_3COOH$, $H_2SO_4$, DNT, DMMP, DNA sequences, RNA, and proteins such as IgG and prostate-specific antigen.

In another embodiment, the disclosure provides an electronic chemical sensor comprising: a) a semiconductor transducer; and b) a functional shell having an atom-thick backbone with one or more types of covalently attached functional groups in a tube-in-a-tube configuration, and wherein the covalently attached functional groups prevent non-specific binding of interfering chemicals.

In another embodiment, the disclosure provides an electronic chemical sensor comprising: a) a semiconductor transducer; and b) a functional shell having an atom-thick backbone with one or more types of covalently attached functional groups in a tube-in-a-tube configuration, wherein the tube-in-a-tube configuration is fabricated from double-walled carbon nanotubes by covalent functionalization of the outer wall.

In another embodiment, the disclosure provides an electronic chemical sensor comprising: a) a semiconductor transducer; and b) a functional shell having an atom-thick backbone with one or more types of covalently attached functional groups in a tube-in-a-tube configuration, wherein the sensor is fabricated from one individual tube-in-a-tube.

In another embodiment, the disclosure provides an electronic chemical sensor comprising: a) a semiconductor transducer; and b) a functional shell having an atom-thick backbone with one or more types of covalently attached functional groups in a tube-in-a-tube configuration, wherein the sensor is fabricated from a thin-film of networked tube-in-a-tubes.

In another embodiment, the disclosure provides an electronic chemical sensor comprising: a) a semiconductor transducer; and b) a functional shell having an atom-thick backbone with one or more types of covalently attached functional groups in a tube-in-a-tube configuration, wherein the electronic chemical sensor is modulated by a gate electrode.

In another embodiment, the disclosure provides an electronic chemical sensor comprising: a) a semiconductor transducer; and b) a functional shell having an atom-thick backbone with one or more types of covalently attached functional groups in a tube-in-a-tube configuration, wherein the electronic chemical sensor is directly gated by the surface functional groups or chemical changes due to surface binding events.

In another embodiment, the disclosure provides an electronic chemical sensor comprising: a) a semiconductor transducer; and b) a functional shell having an atom-thick backbone with one or more types of covalently attached functional groups in a tube-in-a-tube configuration, and wherein the covalently attached functional groups are chemically converted to attach polynucleotides, antibodies, or other functional groups that specifically recognize a DNA, RNA, protein, or chemical. In another embodiment, the chemical is an amine- and nitro-containing explosives (in vapor or liquid phase). In another embodiment, the amine- and nitro-containing explosives are selected from the group consisting of TNT, nitroglycerin, cyclotetramethylene-tetranitramine, hexamethylene triperoxide diamine (HMTD), urea nitrate, cyclonite, hexahydro-1,3,5-trinitro-1,3,5-triazine (RDX), and 4-dimethylaminophenylpentazole.

In another embodiment, the disclosure provides a method of removing covalently attached functional groups from the functional shell of a tube-in-a-tube configuration, the method comprising shining a laser or other light source at the tube-in-a-tube configuration, wherein the laser or other light source is resonant with the inner tube. In another embodiment, the functional shell of a tube-in-a-tube configuration is optically patterned.

In another embodiment, the disclosure provides a method of removing covalently attached functional groups from the functional shell of a tube-in-a-tube configuration, the method comprising shining a laser or other light source at the tube-in-a-tube configuration, wherein the laser or other light source is resonant with the inner tube, and wherein the inner tube of the tube-in-a-tube configuration is semiconducting or metallic.

In another embodiment, the disclosure provides a method of removing covalently attached functional groups from the functional shell of a tube-in-a-tube configuration, the method comprising shining a laser or other light source that is resonant with the inner tube of the tube-in-a-tube configuration, wherein the removing attached functional groups from the functional shell of a tube-in-a-tube configuration generates conductive pathways from an insulating film. The tube-in-a-tube structures that constitute the thin film of this disclosure are insulating from each other because the functional groups prevent electrical contact at tube-tube junctions. Writing with a laser resonant with the inner tube generates conducting pathways on the insulating tube-in-a-tube thin film due to the patterned intertube contact. Using this method, electrode or circuit design from metallic and semiconducting inner tubes, respectively, can be designed for an electronic chemical sensor comprising: a) a semiconductor transducer; and b) a functional shell in a tube-in-a-tube configuration.

In another embodiment, the disclosure provides a method of removing covalently attached functional groups from the functional shell of a tube-in-a-tube configuration, the method comprising using a laser or other light source that is resonant with the inner tube of the tube-in-a-tube configuration, wherein the tube-in-a-tube configuration comprises double-walled carbon nanotubes.

In another embodiment, the disclosure provides a method of removing covalently attached functional groups from the functional shell of a tube-in-a-tube configuration, the method comprising using a laser or other light source that is resonant with the inner tube of the tube-in-a-tube configuration, wherein the removing attached functional groups from the functional shell of a tube-in-a-tube configuration generates an electrical intertube pathway enabling an electronic device, e.g., a circuit board, to be patterned with semiconducting and/or metallic components based on the inner tube properties.

The disclosure provides simultaneous high sensitivity and chemical selectivity in outer-wall selectively functionalized double-walled carbon nanotube (DWCNT) and tube-in-a-tube-based thin film transistors (TFTs). The outer wall of DWCNTs was selectively functionalized using diazonium chemistry to provide a variety of terminating groups, including —COOH, —OH, —$CH_3$, —$NO_2$. Because the inner tubes are hermetically sealed by the functional outer wall, non-specific binding can be significantly reduced. The transduction performance of the inner tube can be superior to other structures such as embedding SWCNTs in a functional coating or functionalized silicon nanowires, since the functionalized outer wall provides complete surface coverage and is only one atom-thick. This double wall structure thus makes it possible to fabricate high performance chemical sensors with tailored surface chemistry to simultaneously achieve ultrahigh sensitivity and selectivity along with long-term stability.

By eliminating the need of a physical gate, the electronic chemical sensor of the present disclosure comprising a functional shell in a tube-in-a-tube configuration can be fabricated in a way as straightforward as a two-terminal resistor, but retains the high sensitivity of a field effect transistor (FET). This simplified design facilitates the fabrication of high density device arrays for multiplexing diagnostics. The simplified device architecture, enabled by tube-in-a-tube configuration, can make it also possible to replace the doped silicon substrate, which is often used for the dual purpose of substrate and gate, with a more flexible and inexpensive substrate such as plastics and paper, allowing electrical sensor arrays to be produced at extremely low cost by scalable, high throughput techniques such direct printing or writing (Dungchai et al., *Analytical Chemistry* 2009, 81 (14), 5821-5826; Martinez et al., *Analytical Chemistry* 2010, 82 (1), 3-10; and Martinez et al., *Angewandte Chemie-International Edition* 2007, 46 (8), 1318-1320).

Covalent attachment of probe molecules in a tube-in-a-tube structure overcomes a major limitation of SWCNTs-based FET sensors, which, due to electron scattering, is limited to non-covalent strategies (Goldsmith et al., *Science* 2007, 315 (5808), 77-81). The much improved stability of the covalent C—C bond over $\pi$-$\pi$ stacking (Blanksby et al., *Accounts of Chemical Research* 2003, 36 (4), 255-263 and Sinnokrot et al., *Journal of the American Chemical Society* 2002, 124 (36), 10887-10893) is over an order of magnitude higher in energy and is important for concerns revolving around device stability, probe robustness for point-of-care usage and preventing cross-talk in multiplexed arrays (Wang et al., *Journal of the American Chemical Society* 2011, 133 (29), 11181-11193). The chemical sensors of this disclosure have demonstrated exceptional long-term device stability (6 months) and rapid response times (within seconds) alongside its high simultaneous sensitivity and selectivity.

Device integration of nanomaterials is typically more challenging because lithography is based on top-down approaches. With the tube-in-a-tube structure, the configuration makes it possible to fabricate electronic devices from thin films by direct laser writing. This new nanofabrication technique can be disruptive because of its direct-write nature and seamless integration of synthetic nanostructures in functional devices. Although this can be extended to single tube-in-a-tube-based sensors, thin films are potentially more technologically important owing to their broader dynamic ranges, higher scalability, and better reproducibility (Sun et al., *Nature Nanotechnology* 2011, 6(3), 156-161 and Kang et al., *Nature Nanotechnology* 2007, 2 (4), 230-236). Particularly, device-to-device variations, due to structure distribution or dopant fluctuation in increasingly small structures, can be minimized by statistical averaging while retaining excellent electron mobilities needed for high sensitivity (Cao et al., *Advanced Materials* 2009, 21 (1), 29-53).

By combining the protected electrical properties of the inner tube with robust surface chemistry, a tube-in-a-tube configuration offers new opportunities for device innovation and electrical probing of a vast array of biological systems and molecule-surface interactions such as protein-substrate interactions. The tube-in-a-tube structure allows the design and fabrication of novel electronic architectures that are inherently sensitive to local molecular environment. Chemical functionalization further adds a new dimension of analyte selectivity. For example, this tube-in-a-tube structure opens the opportunity to resolve the evolution of covalent chemistry on a carbon lattice and their impacts on the electronic properties in a FET configuration. This type of study was previously impossible with SWCNT FETs due to electron scattering by the covalently attached functional groups.

A tube-in-a-tube combines the key structural features critical for ultra-sensitive, ultra-selective, and multiplexing electrical detection of biomolecules. For example, a tube-in-a-tube retains the high mobility and surface features of SWCNTs, while eliminating non-specific interactions through a covalently functionalized outer shell. The robust, covalent surface chemistry also facilitates development of stable and multiplexing capabilities, which is difficult with SWCNTs. Although the chemistry can also be realized with bi-layer graphene, gating is difficult with graphene because graphene is not an intrinsic semiconductor (Meric et al., *Nature Nanotechnology* 2008, 3 (11), 654-659 and Quhe et al., *Npg Asia Materials* 2012, 4). With an atom-thick structure, the semiconducting channel in a tube-in-a-tube has every constituent atom on the surface, making it inherently sensitive due to the highest possible surface-to-volume ratio. Hence, a tube-in-a-tube combines the sensitivity of SWCNTs, selectivity and multiplexing capabilities of silicon nanowires, and offers more due to the structural and chemical stability of carbon and surface chemistry.

The tube-in-a-tube also makes it possible to remove the restraints of conventional thin-film transistor sensors, which require a third electrode to gate the current between source and drain. Instead, a tube-in-a-tube can be gated completely by the covalently attached surface functional groups in thin film structures. This capability is enabled by the high density of charged functional groups made possible through a tube-in-a-tube and the effective intertube contact.

By eliminating the need of the gating electrode, high density arrays of tube-in-a-tube-based sensors can be fabricated on flexible and inexpensive substrates such as paper by inkjet printing or laser writing. This is more challenging for conventional FET sensors because the gate electrode, applied directly through liquid or the back of the substrate, is difficult to integrate (Tey et al., *Small* 2010, 6 (9), 993-998 and Pacios et al., *Nanoscale* 2012, 4 (19), 5917-5923).

The tube-in-a-tube structure further makes it possible to remove the surface functional groups using a laser tuned to resonance with the inner tube. By direct laser writing and re-functionalization, multiplexing sensor arrays can be created in remarkably simple steps.

Figure 12:
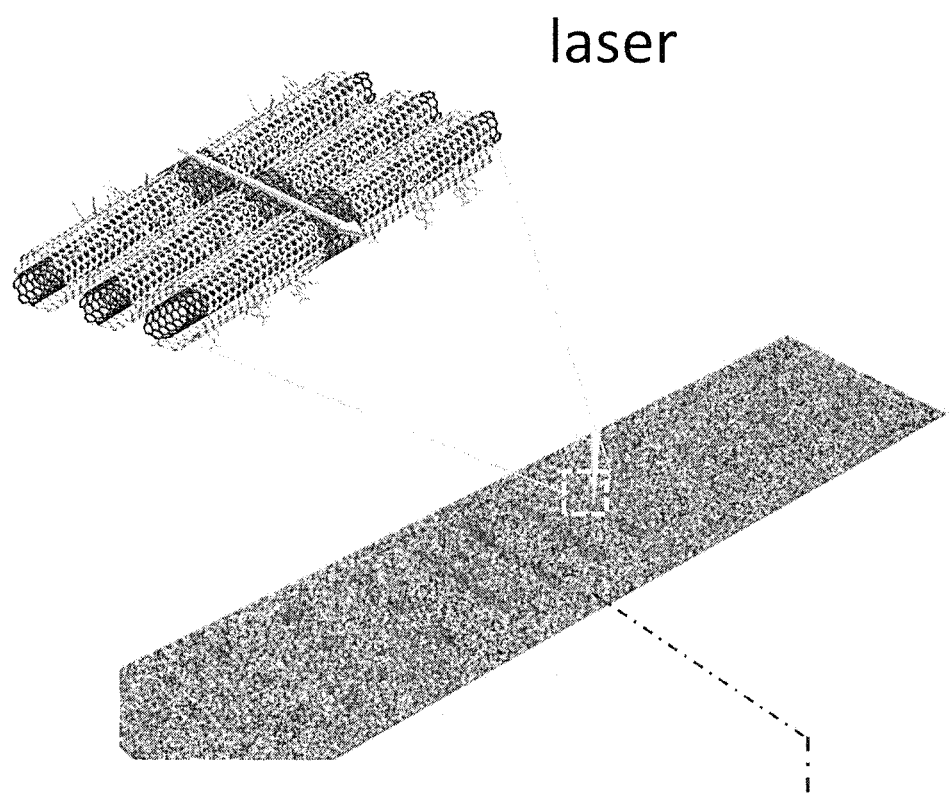
FIG. 12 is an illustration of the electrical conductivity of laser patterned DWCNT channels. (a) Schematic illustration of optical patterning on a Tube^2 network; the inset is the enlarged scheme showing the inner tube-annealed outer wall conducting pathway. (b) Optically selective encoding of Tube^2. The Tube^2 thin film was patterned with one laser and read with Raman spectroscopy. Two laser lines, 532 nm and 633 nm, one of which was in resonance with the inner tube, were used for the writing and reading, leading to four structure combinations. In the Raman spectra, Tube^2 were shown in dashed lines and laser annealing converts Tube^2 to DWCNTs, as shown in solid lines. The molecular models shown are the simplest scenario with only three Tube^2.
Figure 13:
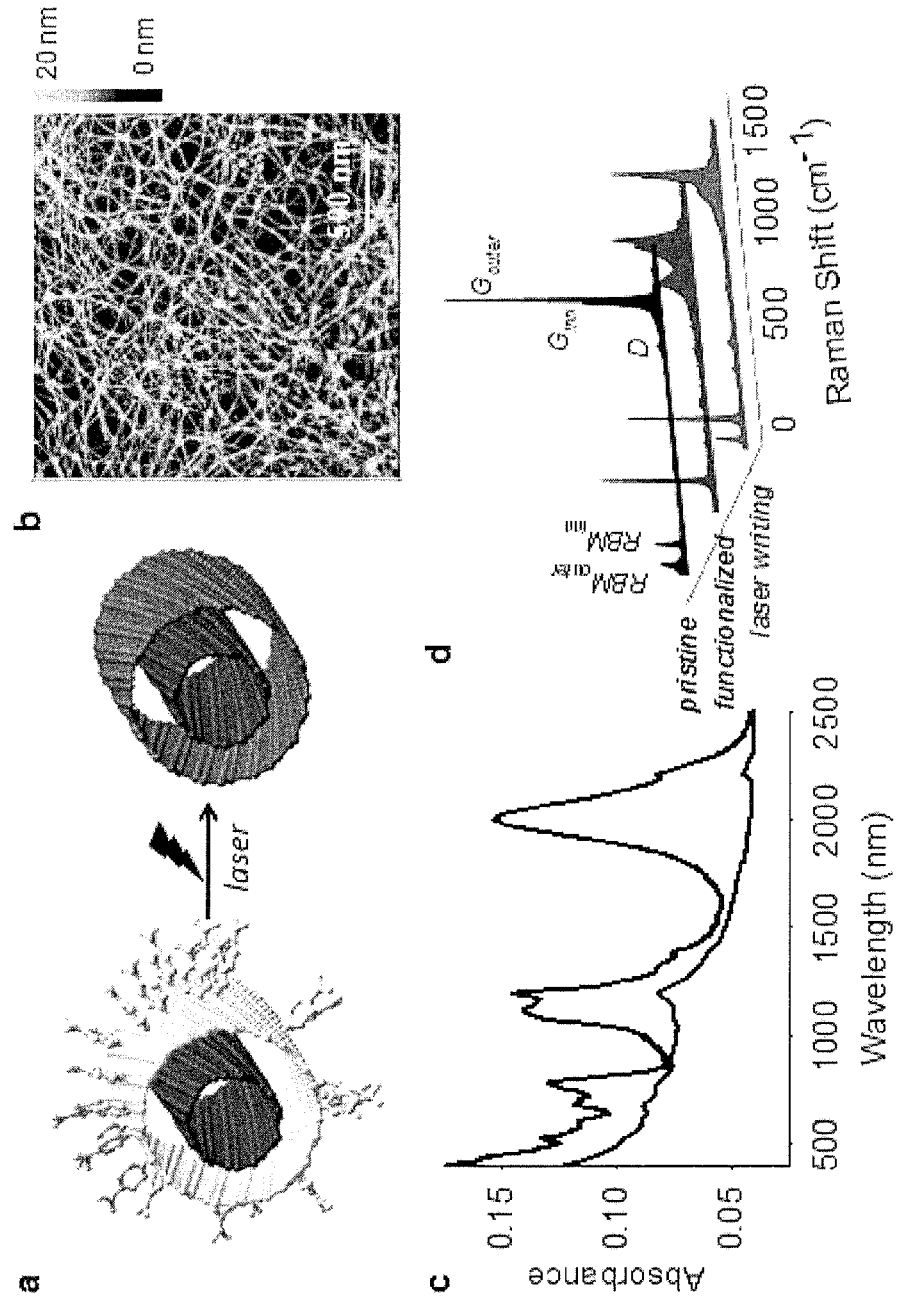
FIG. 13 is a series of illustrations of the laser writing of C6H4Br-Tube^2 networks. (a) Schematic illustration of laser annealing of Tube^2. (b) AFM image of a Tube^2 network on a quartz substrate. (c) Visible-NIR absorption spectra of DWCNTs and Tube^2 films on quartz substrates. (d) Raman spectra showing DWCNTs, Tube^2, and laser annealed Tube^2 (which converts Tube^2 to DWCNTs). Excitation line is 532 nm.

Aryl-functionalized groups can be covalently attached to DWCNTs individually dispersed in solution. The degree of functionalization can be characterized with established Raman spectroscopy, absorption spectroscopy as well as TGA and XPS (Piao et al., *Journal of Physical Chemistry Letters* 2011, 2, 1577-1582; Huang et al., *Journal of the American Chemical Society* 2013, 135, 2306-2312; and Deng et al., *J. Mater. Chem.* 2011, 21, 18568-18574) Thin films of a tube-in-a-tube can be prepared from solution containing the pre-functionalized DWCNTs using an established filtration-and-transfer procedure (Huang et al., *Journal of the American Chemical Society* 2013, 135, 2306-2312 and Wu et al., *Science* 2004, 305, 1273-1277). A confocal Raman microscope (Horiba Jobin Yvon LabRAM ARAMIS) can be used to create desired patterns and characterized with in situ Raman mapping and electrical measurements. The optically patterned region can then be re-functionalized with a diazonium salt such as 2,3,5,6-fluoro-4-carboxylbenzenediazonium tetrafluoroborate, whose carboxyl group can be activated using EDC and NHS to allow attachment of the desired probe such as anti-PSA Fab fragments (Burgener et al., *Bioconjugate Chemistry* 2000, 11 (6), 749-754 and Ionescu et al., *Biosensors & Bioelectronics* 2007, 23 (4), 549-555). FIG. 12 illustrates that optical excitation of the inner tube of a tube-in-a-tube, which is functionalized with $C_6H_4Br$, causes de-functionalization of the outer wall.

Figure 14:
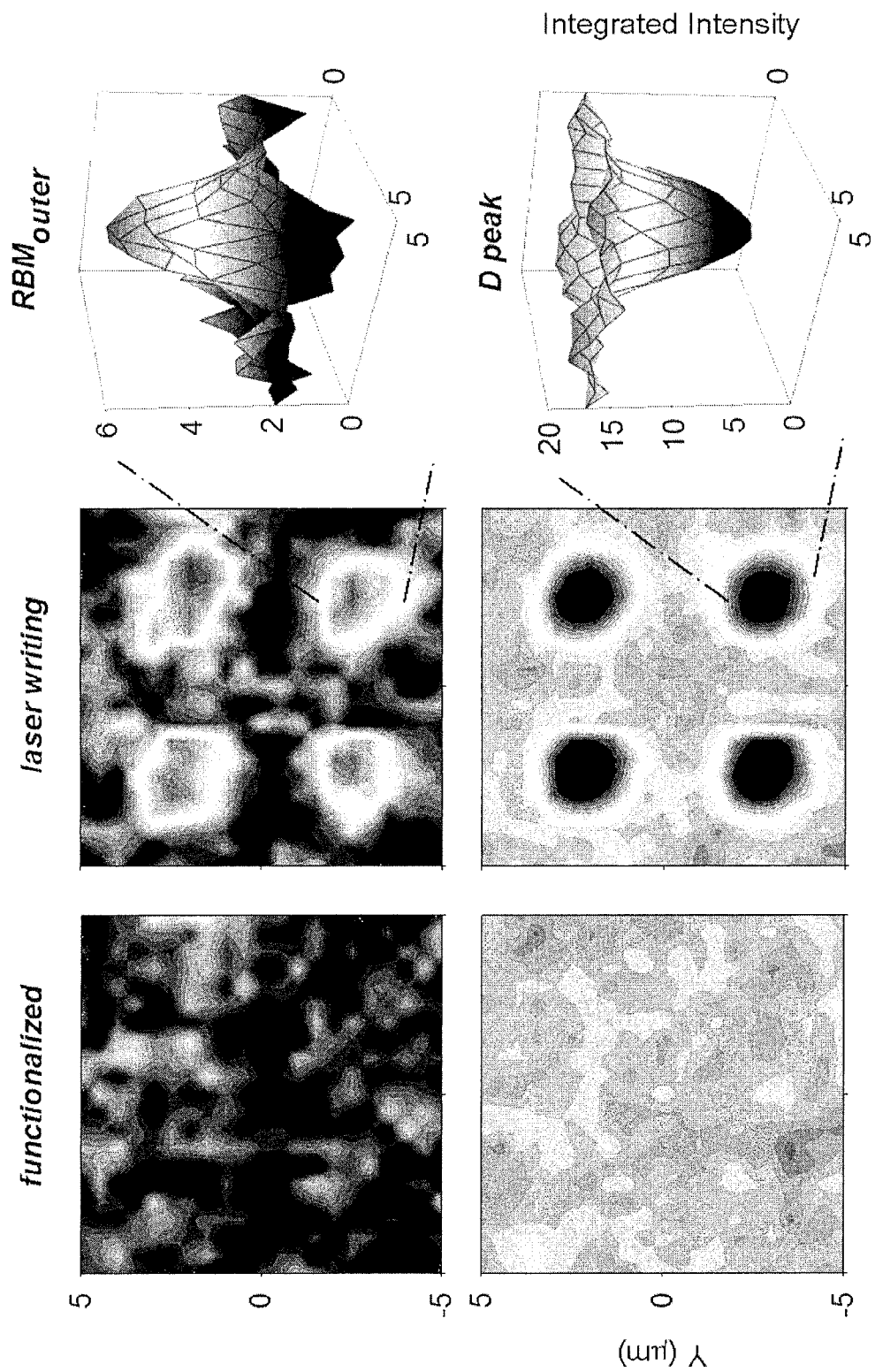
FIG. 14 is a series of illustrations of laser patterned dot arrays confirmed by Raman mapping. Micro Raman mappings showing the creation of a 2×2 dot array by direct-write laser patterning on a Tube^2 thin film. The laser used was 532 nm (50 mW/μm$^2$) for 1 second per spot. Shown are the integrated Raman intensity of $RBM_{inner}$, D peak and $G_{outer}$ before and after laser annealing. Raman spectra were recorded at 0.5 μm steps over a 10 μm×10 μm area. Reading with Raman was performed at 0.5 mW/μm$^2$

The patterning capability of this technique has also been demonstrated. FIG. 14 shows a 2×2 array of 2.5 μm dots written on a tube-in-a-tube thin film using a 532 nm laser beam with 50 mW/μm$^2$ power density. Selective removal of functional groups from outer tubes is confirmed by the recovery of the RBM and G peaks of the outer tubes and diminished D band.

Figure 15:
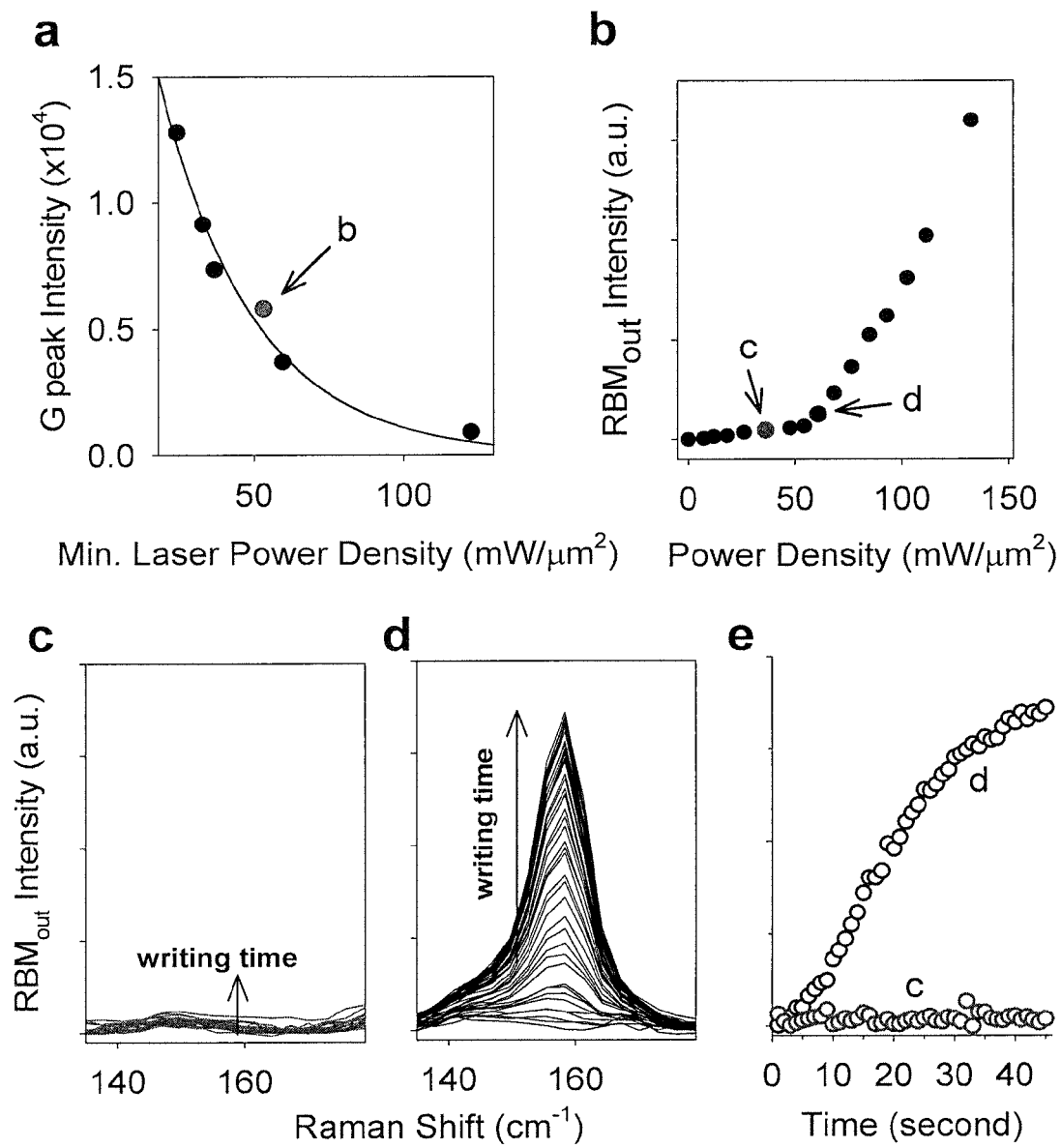
FIG. 15 is two line graphs of critical power density. (a) The minimum power density of laser required for patterning a Tube^2 film of varying thickness, which is approximately proportional to the Raman intensity of the G-peak, measured using laser intensity well below the threshold energy. (b) Power density vs outer wall RBM intensity of one of the spots in (a) indicated by a pink spot. (c,d,e) Existence of threshold power density for laser patterning of Tube^2 thin films. Pattern creation occurs, as indicated by the recovered RBM intensity of outer walls. Shown is Raman spectral evolution of the RBM of outer walls as a function of laser irradiation time (d) at the threshold power density, 60 mW/μm$^2$ for this film as indicated by blue spot in (b) and (c) at a power density right below the threshold energy (as indicated by red spot in (b)).

Based on power dependence studies, there exists a critical laser power density below which the annealing does not occur (FIG. 15). The existence of this threshold energy can be understood by balanced laser heating and heat dissipation. When the laser power density is higher than the threshold energy, resonant excitation of the inner tubes causes detachment of the functional groups from the outer wall and the recovery increases as a function of the irradiation time. This threshold feature ensures non-invasive, in situ imaging of the patterned structures with Raman spectroscopy and other laser spectroscopic techniques such as confocal fluorescent imaging.

The patterned structure can be re-functionalized with carboxylic acids, which can be used to attach different DNAs or antibodies, to form multiplexed device arrays. This multiplexed patterning is made possible because the covalently attached functional groups protect the residual film areas from functionalization. Using this approach, prototype sensor devices can be fabricated and arrays integrated with patterned electrodes.

A central challenge to applications of nanomaterials such as carbon nanotubes is the heterogeneity in electronic structure. As with SWCNTs, the synthesized tube-in-a-tubes contain approximately two-thirds of semiconductors, and the remaining one-third being metallic. Only the semiconductors can be gated. Experimental results of the present disclosure show that the metallic components can be electrically destroyed to attain high ON/OFF ratios. This method can serve as the alternative approach for device fabrication. A tube-in-a-tube structure can be exploited to create electronic sensor arrays from a mixture of tube-in-a-tube structures by structurally-selective laser writing.

Laser annealing is effective only when the laser wavelength was tuned to resonant wavelengths with the inner tube. As an example, two laser lines were used in the writing: 532 nm, which selectively excites metallic inner tubes; and 632.8 nm, which selectively excite semiconducting inner tubes. In situ Raman spectroscopy suggests that de-functionalization occurs only in outer tubes whose inner tubes are excited by the writing laser. Further experiments suggest that the inner tubes are essential for high contrast laser writing. Controlled experiments with similarly functionalized SWCNTs are not recovered unless at significantly higher laser power.

Unlike the on-chip functionalization, the tube-in-a-tube structures that constitute the thin film of this disclosure are insulating from each other because the functional groups prevent electrical contact at tube-tube junctions. However, writing with 532 nm laser generates conducting pathways on the insulating tube-in-a-tube thin film. The conductivity of a 17 μm wide line increased by more than 600 times upon laser removing of the functional groups. The conductivity increased linearly with the line width. By optically exciting the thin film with sufficiently high powers, functional groups can be selectively removed from DWCNTs whose inner tubes are resonant with the laser. Since in one sample of this disclosure, most semiconductors have distinct excitation bands (600-700 nm) from the metals (400-550 nm), semiconducting channels and metallic electrodes can be patterned simultaneously using two different lasers, such as a 633 nm laser for semiconductors and a 532 nm for metals. To investigate this possibility, tube-in-a-tube-based sensors can be fabricated without electrical breakdown and electrode fabrication steps to create semiconducting circuits and metallic electrodes using only a functionalized DWCNT thin film. Characterization of these devices are compared with those fabricated with the conventional lithography protocols.

Definitions

The term "semiconductor transducer" as used herein refers to a semiconducting circuit used or usable for sensor applications.

The term "tube-in-a-tube" or "Tube^2" as used herein refers to a molecular cylinder of sp2 bonded carbon nested in a chemically tailored functional shell. This structure is created from double-walled carbon nanotubes through outer wall-selective covalent chemistry (Brozena et al., *Journal of the American Chemical Society* 2010, 132, 3932-3938; Piao et al., *Journal of Physical Chemistry Letters* 2011, 2, 1577-1582; Huang et al., *Journal of the American Chemical Society* 2013, 135, 2306-2312; and Shen et al., *Nanoscale* 2011, 3, 503-518). In one embodiment, each double-walled nanotube consists of exactly two SWCNTs, with diameters of about 0.86 nm and about 1.61 nm, one nested within another.

The term "interfering chemicals" as used herein refers to molecules that are not the intended target analyte, which may if non-specifically bound to the surface will yield a false positive or negative signal.

The term "gate electrode" as used herein refers to a third terminal used to modulate the conductance of a transistor by enhancing or depleting carriers through the means of the field-effect.

The term "carbon nanotube" or "CNT" as used herein refers to an allotropic form of carbon with a cylindrical nanostructure (see, for example, Baughman et al., *Science* 297:787-192 (2002)).

CNTs are differentiated by their chiral vector (n, m). For the purpose of the present disclosure, CNTs can be categorized into different types, e.g., according to their diameter, wall number, and/or electrical properties. For single-walled carbon nanotubes, CNTs can also be differentiated according to their chirality.

The term "chirality" as used herein refers to a SWCNT having discrete (n,m) values.

The term "composition" or "mixture" as used herein in refers to a population of CNTs comprising more than one type, e.g., single-walled, double-walled, metallic, semiconducting, small-diameter, larger-diameter, and/or chirality.

The term "covalently functionalized CNT" as used herein refers to CNT having surface functional groups attached to the nanotube carbon sidewall through a covalent bond.

The term "about," as used herein, includes the recited number±10%. Thus, "about 10" means 9 to 11.

EXAMPLES

Example 1

Tube^2 Thin Film Transistors

Figure 2:
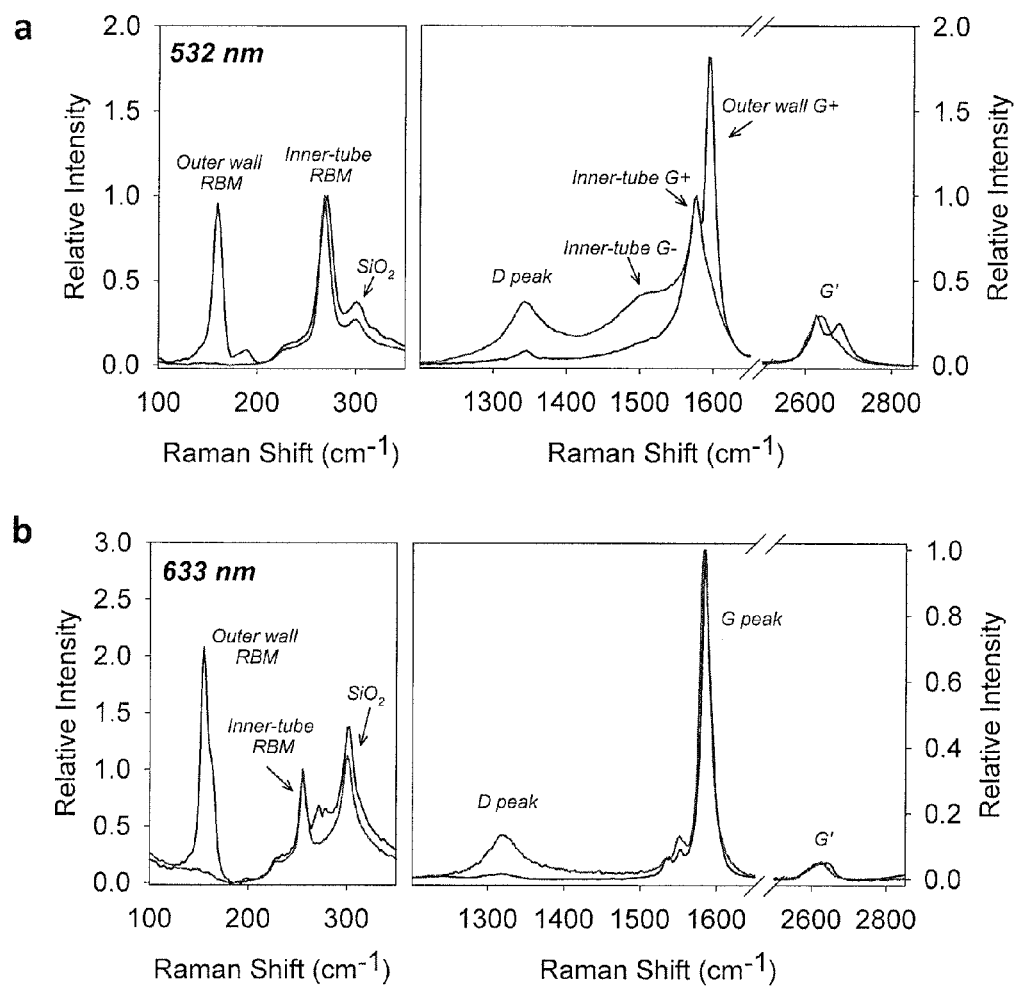
FIG. 2 is Raman spectra of DWCNT thin films before (black line) and after covalent functionalization with —$C_6H_4COOH$ groups (red line) for excitation lines of a) 532 nm and b) 633 nm showing evidence of outer wall selective covalent functionalization.
Figure 9:
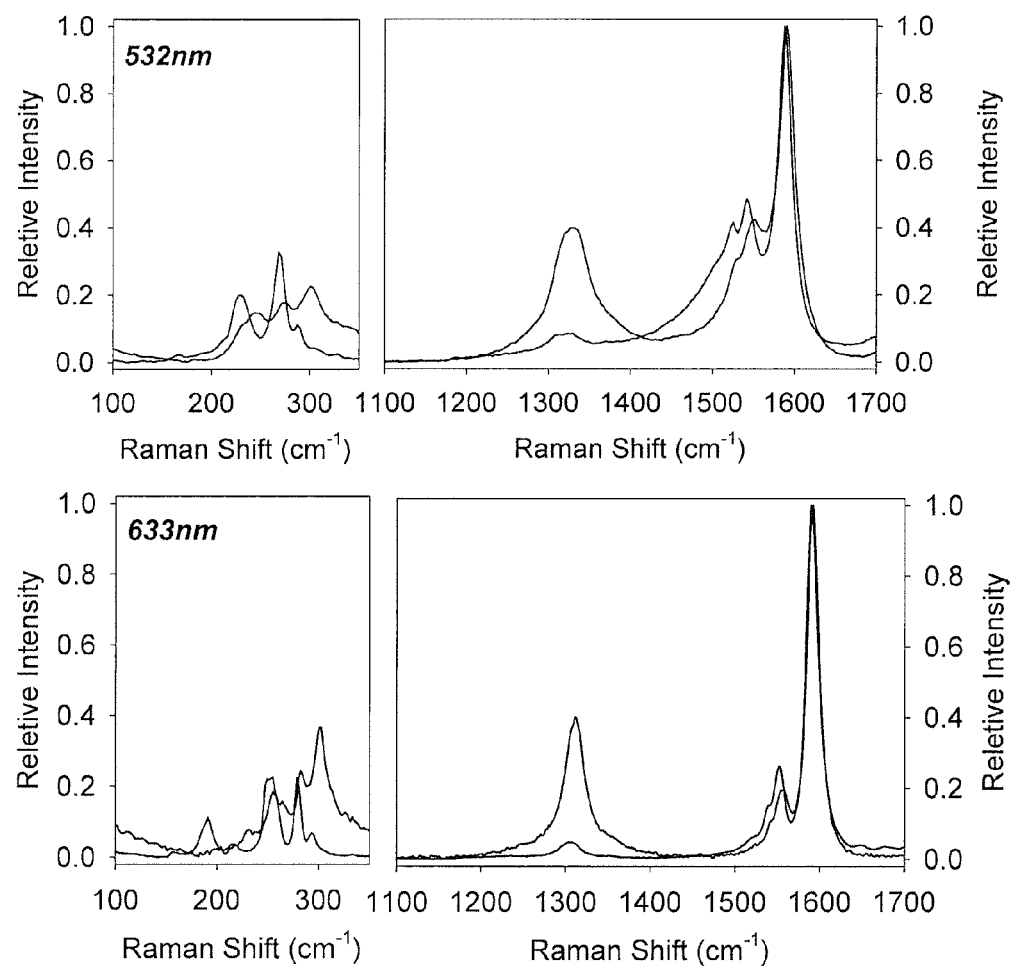
FIG. 9 is Raman spectra of SWCNT thin films before (black line) and after covalent functionalization with —$C_6H_4COOH$ groups (red line) for excitation lines of a) 532 nm and b) 633 nm.

Tube^2 thin film transistors were fabricated from high-purity DWCNTs (Green et al., *Nat. Nanotechnol.* 2009, 4, 64) and their device performance was compared with SWCNTs and multi-walled carbon nanotubes (MWCNTs). The DWCNT TFT devices were covalently functionalized with —$C_6H_4COOH$ functional groups by reacting with 4-carboxylbenzenediazonium tetrafluoroborate in the dark at room temperature. Successful covalent functionalization of the outer wall was confirmed by comparative Raman spectroscopy studies of DWCNTs and SWCNTs before and after the functionalization (FIGS. 2 and 9). After functionalization, the disorder mode (D band) around 1310 $cm^{-1}$ appeared, signifying covalent modification of the nanotube sidewalls. In the functionalized DWCNTs, the radial breathing mode (RBM) of the inner tube (200-400 $cm^{-1}$) remained intact while that of the outer wall (under 200 $cm^{-1}$) completely disappeared, unambiguously confirming selective covalent functionalization of the outer wall. There was an increase in the $G^-$ mode of inner tubes after functionalization, whose origin is not clear but may be due to a weakened wall-to-wall interaction due to outer wall functionalization.

Figure 3:
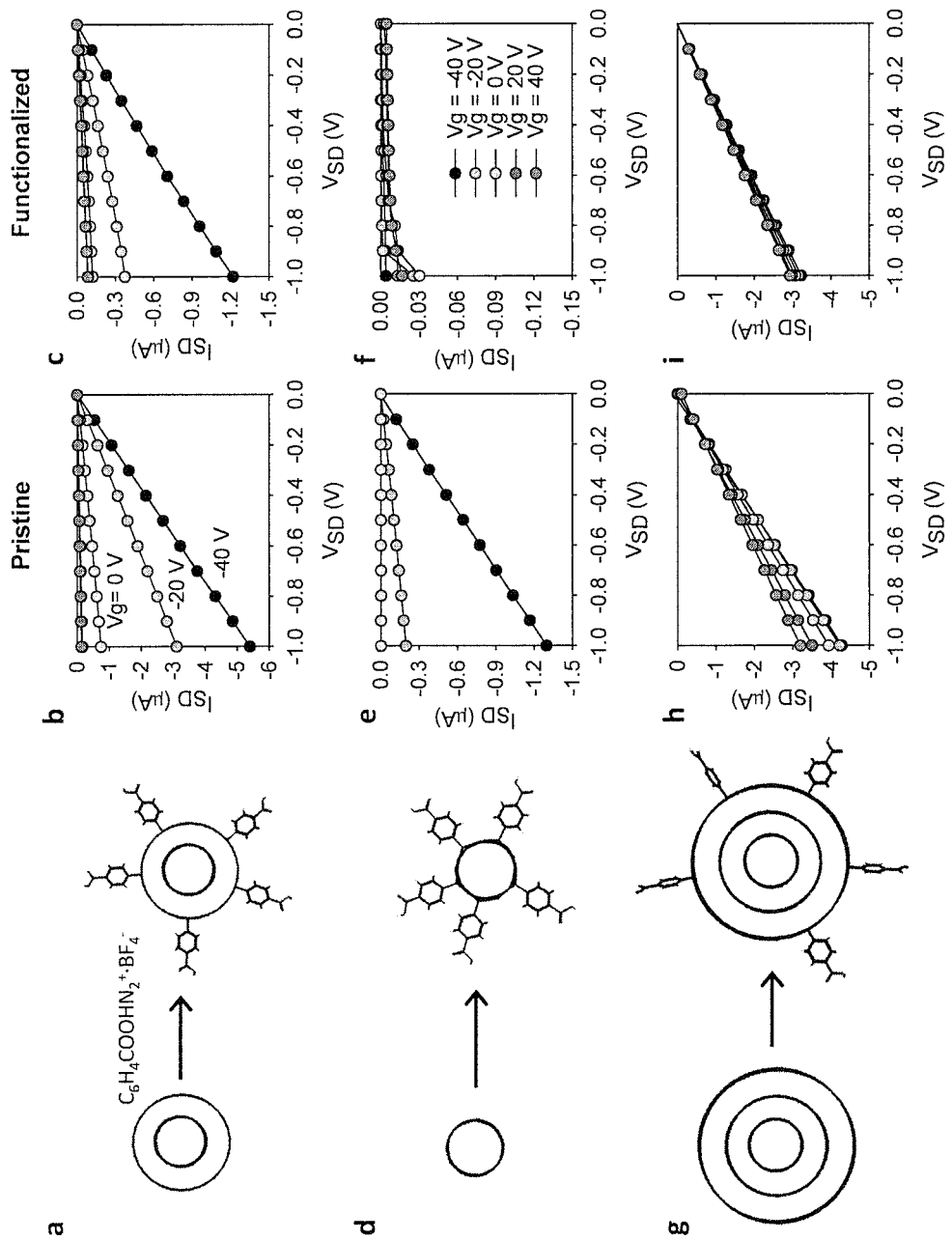
FIG. 3 is series of illustrations and line graphs showing source-drain I-V curves of a Tube^2 thin film transistor having persistent transistor properties in contrast to their DWCNT precursors and single-walled and multi-walled counterparts.

FIG. 3 shows the I-V characteristics of the p-type DWCNT TFTs (FIGS. 3a and 3b) in comparison with similarly fabricated p-type SWCNT TFTs and MWCNT TFTs before and after covalent surface modification with —$C_6H_4COOH$ functional groups. After heavy covalent functionalization, the SWCNT TFT device lost all of its electrical conductivity and transistor characteristics (FIGS. 3e and 3f). In contrast, MWCNTs did not show a significant decrease in electrical conductivity, but the highly metallic nature of the MWCNTs resulted in very low on/off ratios (~1). These MWCNT TFTs, with and without functionalization, exhibit characteristics of resistors rather than that of transistors as evident by their negligible gate amplification effects (FIGS. 3h and 3i); for sensing purposes, it is more desirable to have transistor properties such as a high on/off ratio, which enables detection of charge through gate modulation and amplification of drain current response. For DWCNT TFTs, pristine devices exhibited modest on-current with relatively high on/off ratios. After covalent functionalization, the devices showed 5-10 times lower source-drain current; the source-drain current at $V_g=-40$ V and $V_{SD}=-1$ V was reduced from 5.5 μA to 1.2 μA. However, the source-drain current of covalently functionalized DWCNT TFTs was still on the same magnitude of pristine SWCNTs and their transistor characteristics, most importantly, were retained (FIGS. 3b and 3c). Table 1 compares the on-current, on/off ratio, and chemical selectivity of SWCNT, DWCNT and MWCNT TFTs before and after covalent functionalization. These results confirm that inner tubes in the covalently functionalized double-wall structure uniquely possess desirable semiconductor characteristics.

TABLE 1

Chemical sensing characteristics of Tube^2 TFTs in comparison towards unfunctionalized and functionalized CNT TFTs.

|  |  | On current | On/off ratio | selectivity |
|---|---|---|---|---|
| SWCNT | Pristine | Moderate | High | Low |
|  | Functionalized | Low | N/A | N/A |
| DWCNT |  | High | High | Low |
| Tube^2 |  | High | High | High |
| MWCNT | Pristine | High | Low | Low |
|  | Functionalized | High | Low | Low |

Figure 10:
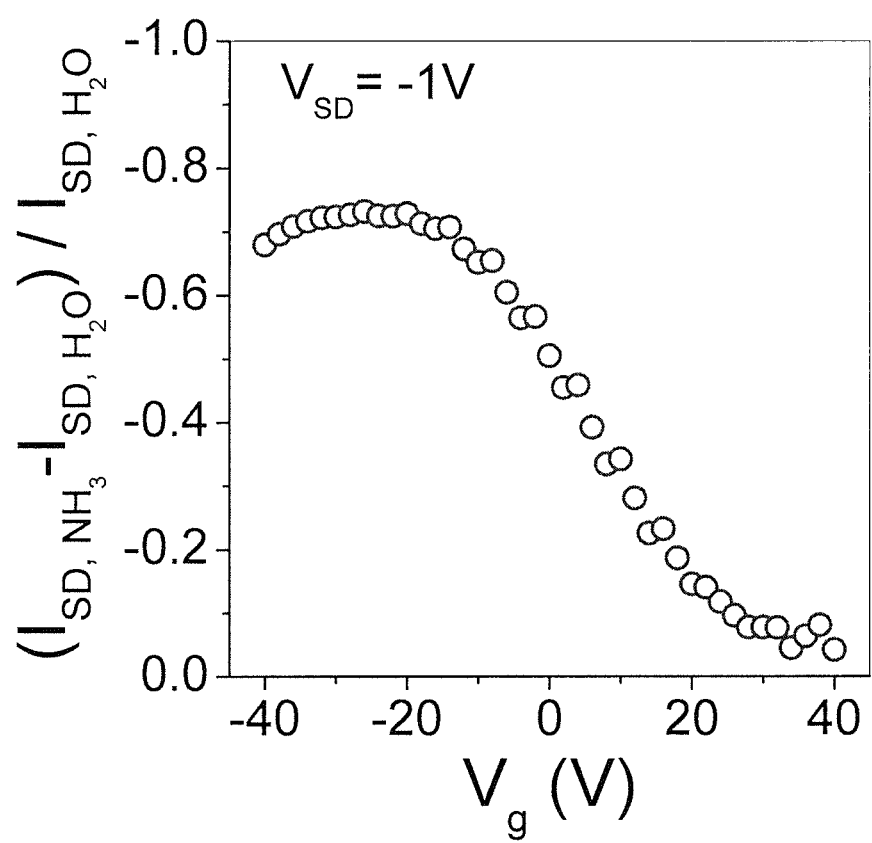
FIG. 10 is a line graph of the relative response of a —COOH functionalized Tube^2 TFT upon exposure to 60 μM $NH_3$ as a function of gate voltage ($V_g$). Higher relative response was observed at negative $V_g$ when the TFT is turned on. When the device was turned off at positive gate voltage much lower response was observed.

Upon exposure to analytes, a p-type CNT TFT with a high on/off ratio has an enhanced response when the device is turned on by applying a negative gate voltage. This phenomena arises because semiconducting CNTs are typically more sensitive to analytes than metallic CNTs (Roberts et al., ACS Nano 2009, 3, 3287). When the TFT is turned on by applying a negative gate voltage, the semiconducting CNTs become conductive. When a high positive gate voltage is applied, the TFT is turned off and the semiconducting CNTs are insulating. A high on/off ratio is indicative of a large ratio of semiconducting CNTs to metallic CNTs in the conduction channel. In this scenario, semiconducting CNTs contribute to the majority of the drain current when the CNT TFT is turned on. Those semiconducting CNTs at the "ON" stage are sensitive to analytes due to charge transfer or trapping effects. The gate modulation effect can thus amplify the responsive component of the drain current and increase sensor response. FIG. 10 shows the normalized gate-dependent response of a functionalized DWCNT TFT upon exposure to 60 μM $NH_3$ as a function of gate voltage. At a $V_g$ of −40 V, the TFT was turned on and about 70% current reduction was observed when the device was exposed to $NH_3$ solution. When the TFT was turned off at a $V_g$ of +40 V, only about 5% current response was observed, illustrating that semiconducting DWCNTs are more responsive to analytes than metallic DWCNTs and the importance of gate amplification effects in a DWCNT TFT sensor.

Figure 4:
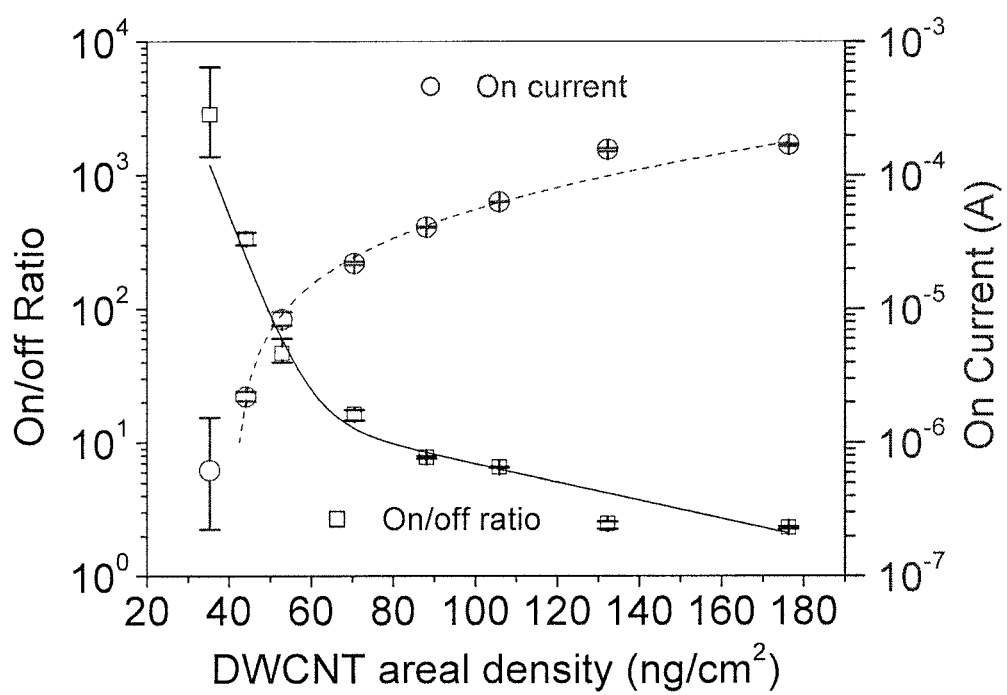
FIG. 4 is a line graph of high source-drain current and on/off ratio can be simultaneously achieved in Tube^2 TFTs at a network density around 50 ng/cm$^2$. The source-drain current at $V_g$=−40 V and $V_{SD}$=−1 V (red) and on/off ratio (black) of the Tube^2 TFTs were plotted as a function of the areal density of Tube^2.

The electrical characteristics of DWCNT TFTs highly depend on the areal density of DWCNTs in the conduction channel, which can be straightforwardly controlled by adjusting the volume and concentration of the DWCNT solution used for filtration. FIG. 4 shows the source-drain current and on/off ratio of DWCNT thin-film TFTs as a function of DWCNT areal density. For each areal density, five devices were fabricated and measured. The DWCNT areal density was calculated by dividing the mass of DWCNTs in the solution by the filtration membrane area.

Figure 5:
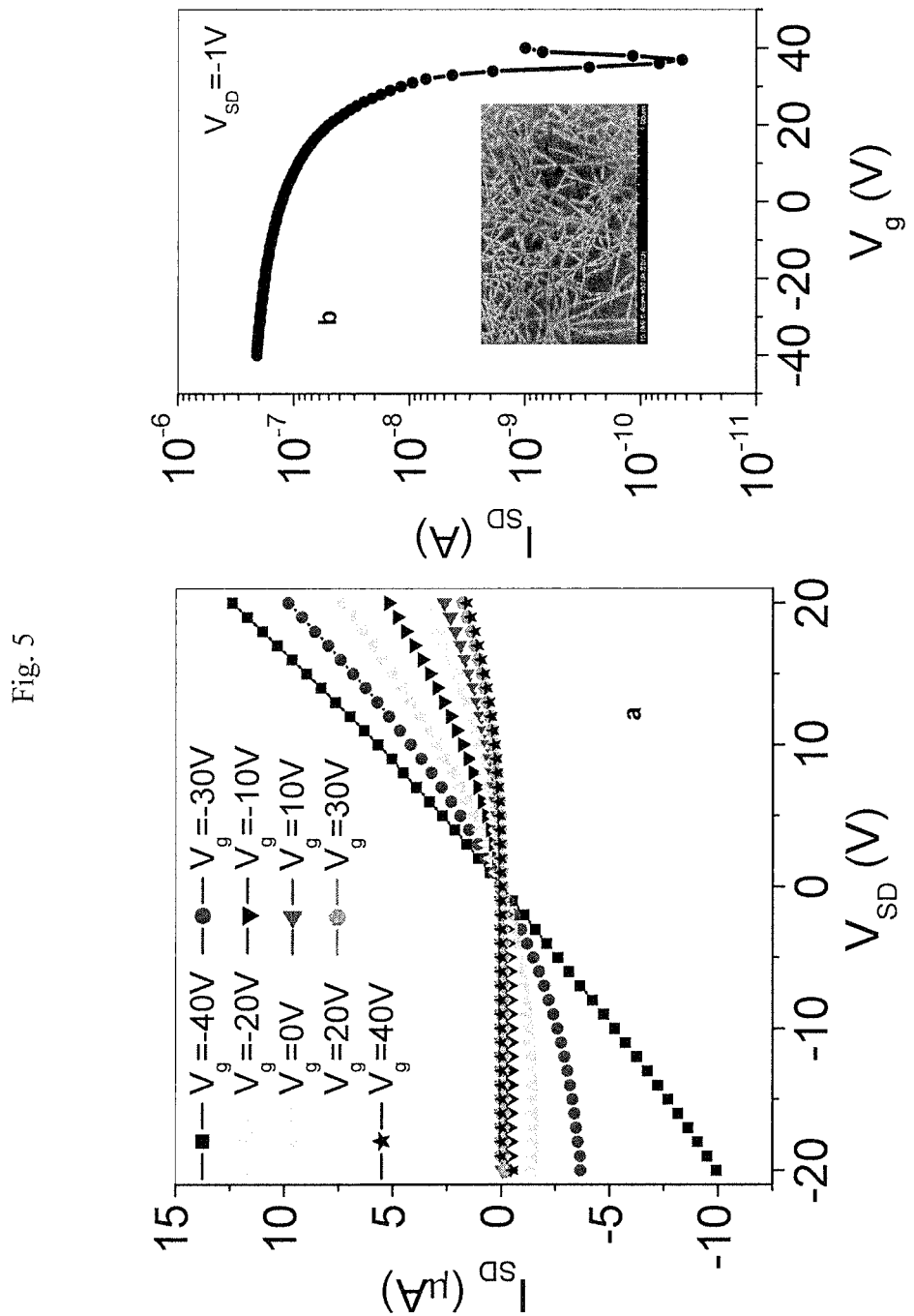
FIG. 5 is two line graphs of (a) Source-drain I-V curves and (b) transfer characteristics of a DWCNT TFT after covalent diazonium functionalization. Inset shows a SEM image of the DWCNT thin film.

It was found that both high on/off ratio and ON current can be simultaneously achieved at DWCNT densities around 50 ng/cm². As shown in FIG. 5, TFTs prepared with a DWCNT areal density of 35 ng/cm² possessed excellent transistor characteristics. Even after functionalization by —$C_6H_5COOH$ groups, this device still exhibited on/off ratio as high as 4,000 when measured in water.

The high on/off ratio is more consistently achieved with low density CNT networks. The low density of the nanotube network is necessary to avoid percolation of metallic nanotubes, which would otherwise electrically short the device. The observed high on/off ratio suggests that the transport is dominated by the semiconducting nanotubes in the network since their conductivity can be effectively modulated by the gate (FIGS. 3 and 5). Although the tube-tube contacts may affect the mobility of the device, they do not dominate the on/off ratio and thus play a secondary role in the sensing mechanism, explaining why the sidewall functionalization dictates the sensor performance. Higher on/off ratio may be achieved if DWCNTs with semiconducting inner tubes can be separated further from those with metallic inner tubes. However, low DWCNT density also leads to low source-drain current due to the smaller quantity of DWCNTs within the network. In this device structure, the source-drain current of DWCNT TFTs with an areal density of 35 ng/cm² can be lower than 1 μA at $V_g$=−40 V and $V_{SD}$=−1 V, as shown in FIG. 4. Vice versa, increasing DWCNT areal density increases the drain current of TFTs, but also decreases the on/off ratio of the device due to the larger number of DWCNTs with metallic inner tubes within the percolated network. In order to obtain sensor devices with desired on-current and reasonable on/off ratio, TFTs with a DWCNT areal density of 53 ng/cm² were chosen and used for the sensor platform.

Figure 6:
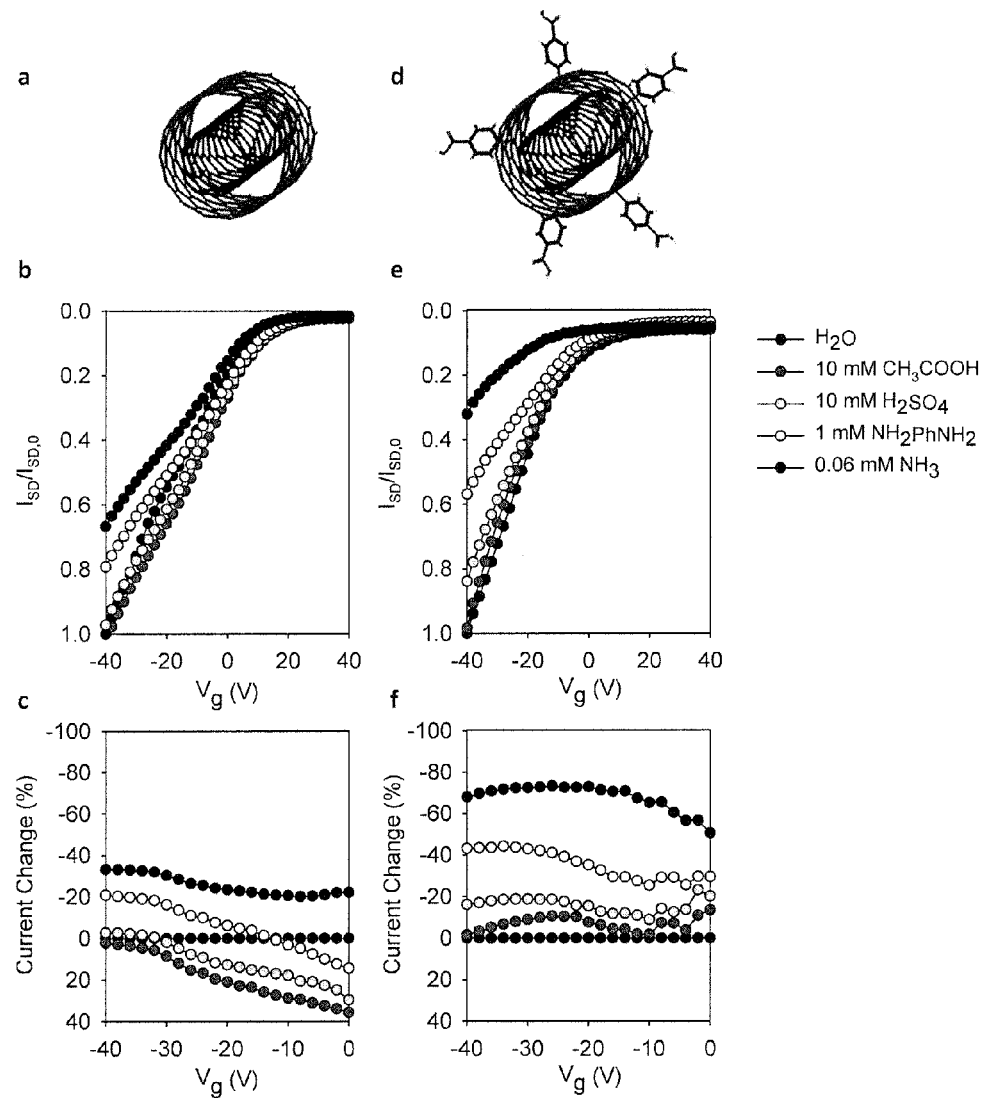
FIG. 6 is series of illustrations and line graphs of Tube^2 TFTs showing higher chemical selectivity than that of DWCNTs. A molecular model of a) DWCNTs and d) Tube^2. Normalized response of (b) a DWCNT TFT and (e) a —$C_6H_4COOH$ functionalized Tube^2 TFT upon exposure to various analytes. The drain current is normalized relative to $I_{SD,0}$, the drain current measured at $V_g$=−40 V, $V_{SD}$=−1 V in $H_2O$. The corresponding current change ($\Delta I_{SD}/I_{SD,H2O}$ at each $V_g$) of (c) the DWCNT TFT and (f) the Tube^2 TFT upon exposure to various analytes.

To demonstrate the application of Tube^2 TFTs for selective chemical detection, outer wall-functionalized and pristine DWCNT TFTs were tested in 0.06 mM $NH_3$, 1 mM $NH_2PhNH_2$, 10 mM $CH_3COOH$, and 10 mM $H_2SO_4$ aqueous solutions. Acids with higher concentrations than $NH_3$ were used in order to show the selective response of the sensors. FIG. 6 compares the change in the transfer characteristics of Tube^2 TFTs in comparison with DWCNT TFTs upon exposure to analyte solutions. The normalized TFT response was plotted as a function of gate voltage. The device with —$C_6H_4COOH$ functionalized Tube^2 exhibited much higher response upon exposure to $NH_3$ and $NH_2PhNH_2$ compared to that of DWCNT TFTs. For the DWCNT TFT, a reduction of about 34% in drain current was observed when the device was exposed to 0.06 mM $NH_3$ solution, while 68%, or twice as much drain current reduction was observed for the Tube^2 TFT. The normalized sensitivity (normalized drain-current change upon exposure to analytes, relative to water, per analyte concentration unit) of this device is as high as 1133% per mM $NH_3$. The sensitivity towards $NH_2PhNH_2$ was also improved by the —$C_6H_4COOH$ functional groups, which indicate that the functional groups may be used provide chemical selectivity. When the functionalized device was exposed to 1 mM $NH_2PhNH_2$ solution, we observed a 43% reduction in the drain current, versus the 22% with the DWCNT TFTs. This nearly two-fold increase in sensitivity can be attributed to the —$C_6H_4COOH$ functional groups on outer walls of the heavily functionalized DWCNTs because of the acid-base interactions between the covalently attached carboxylic acids on the outer sidewall with the amine analytes. Because of this base-acid chemistry, the amine analyte induces a negative charge that reduces the hole density of the p-type carbon nanotube, giving rise to the observed selectivity over acids.

In addition, the normalized sensitivity (1133% per mM) of the functionalized DWCNT TFT upon exposure to 0.06 mM $NH_3$ was 6,000 times higher than the sensitivity to 10 mM acetic acid (0.17% per mM), which demonstrates the chemical selectivity of this novel sensor device based on the chemical interactions between the terminal groups on the outer sidewall with analytes. The diversity of sensor responses observed upon exposure to different analytes shows the selectivity of the sensor device.

Figure 7:
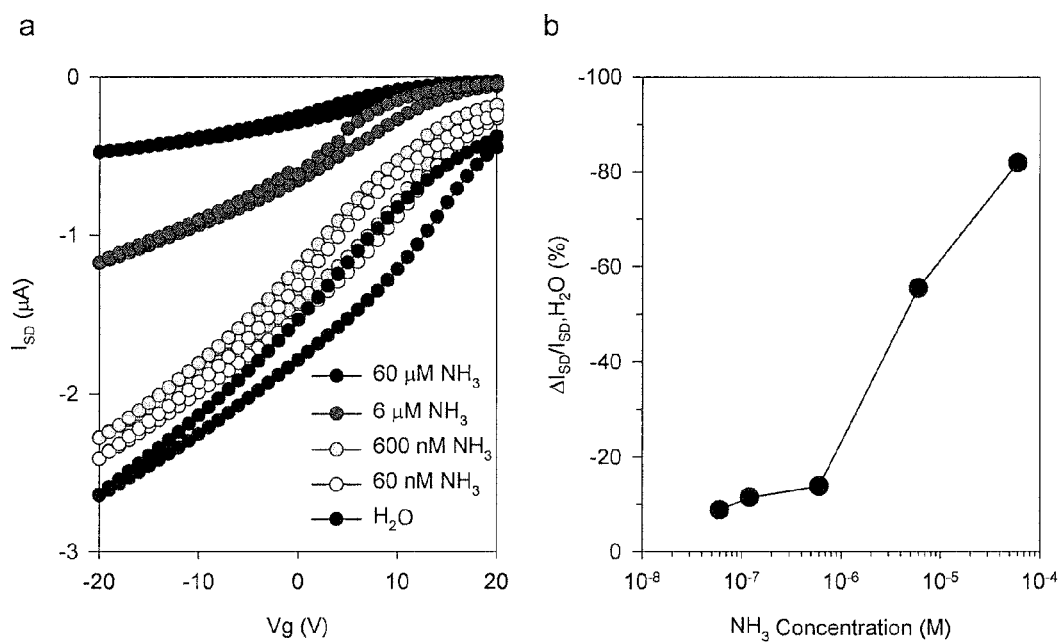
FIG. 7 is two line graphs showing the sensitivity of a Tube^2 TFT. (a) Transfer characteristics and (b) the normalized current change ($\Delta I_{SD}/I_{SD,H2O}$, at $V_g$=−20 V) of a carboxyl group-functionalized Tube^2 TFT as a function of $NH_3$ concentration.
Figure 8:
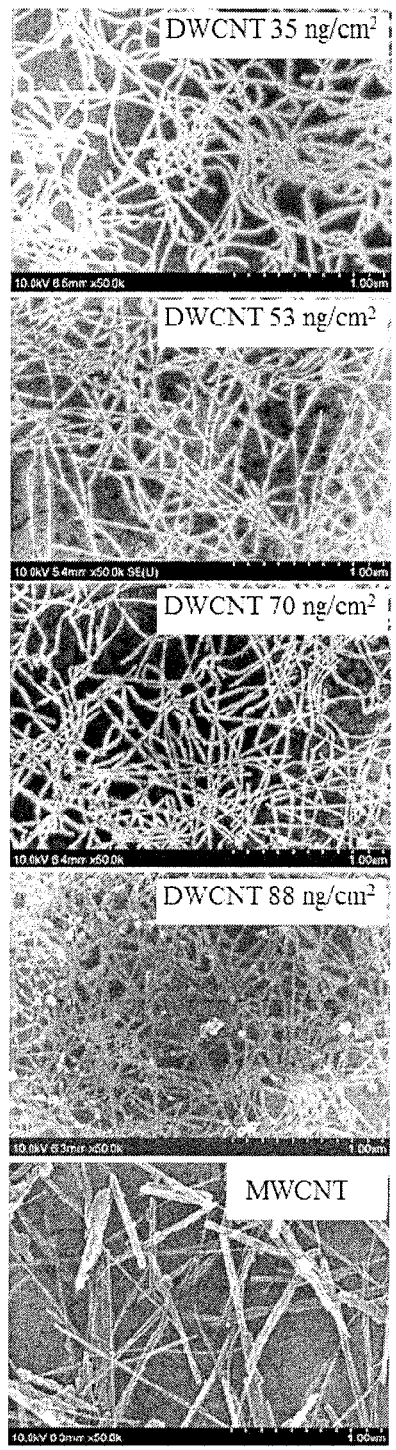
FIG. 8 is a series of five illustrations of SEM images of DWCNT percolated networks at various CNT areal densities and (bottom) MWCNT percolated networks.
Figure 11:
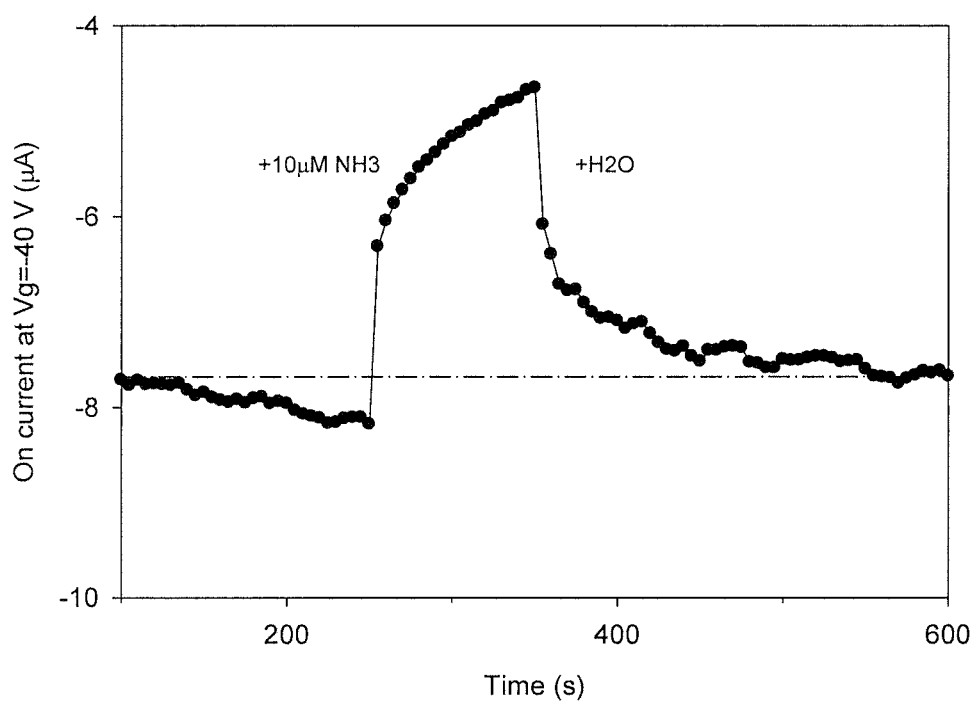
FIG. 11 is line graph of time-dependent measurements showing the reversible increase in ON-current upon introduction of $NH_3$ solutions and replacement with water.

To further demonstrate the capability of Tube^2 for ultrasensitive small molecule detection, a —$C_6H_5COOH$ functionalized DWCNT TFT was tested in diluted $NH_3$ solutions varying from 60 nM to 60 µM. The change of transfer characteristics of this device upon exposure to successively increasing concentrations of $NH_3$ solution is shown in FIG. 7a, with the transfer characteristics measured in nanopure water acting as the baseline. Time-dependent measurements confirm the devices exhibit reversible increase in ON-current upon introduction of $NH_3$ solutions and replacement with water (FIG. 11). FIG. 7b summarizes the corresponding relative conductance change ($\Delta I_{SD}/I_{SD,H2O}$) of this DWCNT TFT as a function of $NH_3$ concentration. Drain current measured at $V_g=-20$ V and $V_{SD}=-1$ V was used as output signal. We note that a $V_g$ of −20 V, instead of −40 V, is chosen here to prevent device damage during repetitive measurements and baseline shift due to gate bias stress effects. $NH_3$ was detected at concentrations as low as 60 nM in water, which is comparable to state-of-the-art TFT sensors based on SWCNTs (Roberts et al., *ACS Nano* 2009, 3, 3287 and Peng et al., *Nano Lett.* 2009, 9, 1626). This value may be further improved by optimizing device structure and utilizing external aid such as pre-concentrators.

In summary, Tube^2 have excellent transistor properties showing an on/off ratio as high as 4,000. With carboxylic acid-functionalized outer walls, the devices displayed a sensitivity of 60 nM (or ~1 ppb), while simultaneously displaying a chemical selectivity as high as 6,000 towards a variety of amine containing analyte molecules over other small molecule analytes. This combined ultrahigh sensitivity and selectivity was made possible by the unique double-wall structure of DWCNTs, which simultaneously enables high sensitivity of SWCNT TFTs and the desirable chemical selectivity by outer wall selective covalent modification. This double-wall device platform thus opens new opportunities for chemical and biological sensing where simultaneously sensitivity and selectivity are desirable for detecting trace analytes of interest within the typically complex chemical environments.

Experimental Section

Nanotube dispersions: High-purity DWCNTs were separated from a CVD-grown sample (Unidym DW411UA) using density gradient ultracentrifugation (DGU) (Green et al., *Nat. Nanotechnol.* 2009, 4, 64). The sorted DWCNTs have an average diameter of 0.86 and 1.61 nm for the inner and outer wall nanotubes, respectively. Purified arc-discharge MWCNTs (n-Tec) were dispersed in aqueous 0.25% sodium dodecyl sulfate. SWCNT solutions were prepared using a procedure derived from a previous publication (O'Connell et al., *Science* 2002, 297, 593). Raw SWCNTs (10 mg, HiPco Lot R0513) were dispersed in a 25 mL of aqueous 1% sodium cholate solution (99.9% Sigma Aldrich) by tip-sonication (MISONIX ultrasonicator operated at a power level of 17 W) in a cooled (15° C.) stainless steel cup for 2 hours. The nanotube dispersion was centrifuged at 64,700 g for 2 hours (Beckman Coulter Optima LE-80K; 70 Ti fixed angle rotor), after which the supernatant was collected. The concentrations of the SWCNT dispersions were adjusted with 1% sodium cholate/$H_2O$ solution to a similar optical absorbance as that of the DWCNT solution (O.D.≈0.032 @ 1000 nm).

Diazonium salts preparation: 4-aminobenzoic acid (4.814 mmol, 99%, Sigma Aldrich) was added to 3 mL of nanopure water in a 10 mL round bottom flask. An aqueous solution of tetrafluoroboric acid (2.68 mL, 48 wt. %, Sigma Aldrich) was then added and the mixture cooled in an ice bath. 670 mg of sodium nitrite (Sigma Aldrich, ≥97.0%) was dissolved in 2 mL of nanopure water and added dropwise to the mixture while stirring. The mixture was allowed to react for 15 minutes. The precipitated diazonium salt was collected and washed with ~200 mL of diethyl ether. The purified salt was dried under vacuum in the dark for 20 minutes. The salt was stored at 4° C. and was used within a week after synthesis.

Raman spectroscopy: Raman spectra were collected on Horiba Jobin Yvon LabRAM Raman microscope (model ARAMIS) with excitation lines that included 532 nm and 633 nm.

UV-vis-NIR absorption spectroscopy: Optical absorption spectra were measured using a PerkinElmer Lambda 1050 UV-Vis-NIR spectrophotometer equipped with a PMT and an InGaAs detector.

Device fabrication: Heavily doped silicon wafers with 300 nm of thermally grown silicon dioxide were used as substrates for all the devices. Prior to the fabrication, the substrates were cleaned by rinsing sequentially with acetone, 2-propanol, ethanol, and water. Bottom-gate top-contact CNT TFTs were fabricated on carbon nanotube thin films that were prepared using a modified filtration method.[33] CNT solutions were filtered through 47 mm mixed cellulose ester (MCE) filter membranes and rinsed with water to remove surfactant. The resulting percolated CNT films along with the filter membranes were placed onto the substrate with the CNT films contacting with silicon oxide surfaces, compressed by applying force, and thermally annealed at 95° C. for one hour to provide the nanotube film with sufficient adhesion to the substrate. After heating and compression, the MCE filter membrane was dissolved using an acetone vapor bath and rinsed with fresh acetone and ethanol. Finally, Cr (10 nm) and Au (50 nm) electrodes were thermally evaporated through shadow masks. Channel length and width are 2.5 and 4.0 mm respectively. For devices with surface functionalization, the CNT TFTs were immersed into 236 mgL$^{-1}$ diazonium solution and slowly stirred for 24 hours in the dark at room temperature, followed by copious rinsing in nanopure water.

Small Molecule Detection: For aqueous sensing measurements, a rectangular region was defined using electronic coating polymer (3M company Novec, EGC-1700) to hold a liquid droplet on each CNT TFT. The polymer was used to protect the Au electrodes from direct contact with the liquid solution. Each sensor was tested sequentially in air, nanopure water, and analyte solutions. Electrical measurements in liquid were performed by placing a droplet (4 µL) of liquid in the designed region between the source-drain electrodes, with the entire channel immersed by the liquid. All DWCNT TFTs exhibited robust performance with stable drain currents in water. No obvious degradation of the CNT TFTs was observed during the measurements. Source-drain current-voltage ($I_{SD}$-$V_{SD}$) curves of the sensors in nanopure water were measured as the baseline for the devices. After the baselines were established, another droplet of analyte solution was added into the pool and I-V curves were measured over time. To recover the sensor devices, sensors were rinsed with copious amounts of nanopure water and then vacuum dried for 24 hours to remove water.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. An electronic chemical sensor comprising:
   a) an atom-thick semiconductor inner tube transducer; and
   b) a functional shell having an atom-thick backbone with a covalently attached functional group selected from the group consisting of $-C_6H_4CH_3$, $-C_6F_4CO_2H$, and $-C_6H_2F_3$, in a tube-in-a-tube configuration.

2. The electronic chemical sensor of claim 1, further comprising an analyte.

3. The electronic chemical sensor of claim 1, wherein the analyte is selected from the group consisting of $NH_3$, $NH_2PhNH_2$, $CH_3COOH$, 2,4-dinitrotoluene, and dimethyl methylphosphonate.

4. The electronic chemical sensor of claim 1, wherein the covalently attached functional groups prevent non-specific binding of interfering chemicals.

5. The electronic chemical sensor of claim 1, wherein the tube-in-a-tube configuration is fabricated from double-walled carbon nanotubes by selective covalent functionalization of the outer wall.

6. The electronic chemical sensor of claim 1, wherein the sensor is fabricated from one individual tube-in-a-tube.

7. The electronic chemical sensor of claim 1, wherein the sensor is fabricated from networked tube-in-a-tubes.

8. The electronic chemical sensor of claim 1 that is modulated by a gate electrode.

9. The electronic chemical sensor of claim 1 that is directly gated by the surface functional groups or chemical changes due to surface binding events.

10. The electronic chemical sensor of claim 1, wherein the covalently attached functional groups are chemically converted to attach polynucleotides, antibodies, or other functional groups that specifically recognize a DNA, RNA, protein, or chemical.

11. The electronic chemical sensor of claim 10, further comprising a chemical, wherein the chemical comprises amine- and nitro-containing explosives.

12. The electronic chemical sensor of claim 11, wherein the amine- and nitro-containing explosives are selected from the group consisting of 2-methyl-1,3,5-trinitrobenzene, nitroglycerin, cyclotetramethylene-tetranitramine, hexamethlene triperoxide diamine, urea nitrate, cyclonite, hexahydro-1,3,5-trinitro-1,3,5-triazine, and 4-dimethylaminophenylpentazole.

* * * * *